(12) United States Patent
Brendel et al.

(10) Patent No.: US 7,235,690 B2
(45) Date of Patent: Jun. 26, 2007

(54) ANTHRANILAMIDES AND METHODS OF THEIR USE

(75) Inventors: Joachim Brendel, Bad Vilbel (DE); Bernard Pirard, Frankfurt (DE); Stefan Peukert, Frankfurt (DE); Heinz-Werner Kleemann, Bischofsheim (DE); Horst Hemmerle, Indianapolis, IN (US)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 525 days.

(21) Appl. No.: 10/132,163

(22) Filed: Apr. 26, 2002

(65) Prior Publication Data

US 2003/0187033 A1 Oct. 2, 2003

(30) Foreign Application Priority Data

Apr. 28, 2001 (DE) ........................ 101 21 003

(51) Int. Cl.
C07C 311/04 (2006.01)
A61K 31/18 (2006.01)

(52) U.S. Cl. .................. 564/91; 564/92; 546/172; 546/265; 546/283.4; 546/333; 546/334; 548/204; 548/309.7; 548/336.1; 548/375.1; 549/493; 514/604; 514/461; 514/427; 514/406; 514/399; 514/394; 514/365; 514/336; 514/332; 514/311; 514/307; 514/357

(58) Field of Classification Search .............. 564/91, 564/92; 546/172, 265, 283.4, 333, 334; 548/204, 548/309.7, 336.1, 375.1; 549/493; 514/604, 514/461, 427, 406, 399, 394, 365, 336, 332, 514/311, 307, 357
See application file for complete search history.

(56) References Cited

U.S. PATENT DOCUMENTS

| | | | | |
|---|---|---|---|---|
| 3,497,529 A | | 2/1970 | Ott ........................ 260/332.2 |
| 4,507,315 A | * | 3/1985 | Ashton et al. ............ 514/396 |
| 5,436,229 A | | 7/1995 | Ruterbories et al. | |
| 5,447,819 A | | 9/1995 | Mooberry et al. | |
| 5,455,348 A | | 10/1995 | Austel et al. | |
| 5,541,343 A | | 7/1996 | Himmelsbach et al. | |
| 5,591,769 A | | 1/1997 | Himmelsbach et al. | |
| 6,140,351 A | | 10/2000 | Arnaiz et al. | |
| 6,221,866 B1 | | 4/2001 | Brendel et al. .......... 514/237.8 |
| 6,380,221 B1 | | 4/2002 | Arnaiz et al. | |
| 6,407,116 B1 | | 6/2002 | Kajino et al. | |
| 6,448,290 B1 | * | 9/2002 | Ohuchida et al. ........... 514/471 |
| 6,498,184 B2 | | 12/2002 | Berendsen | |
| 6,545,055 B1 | | 4/2003 | Zhu et al. | |
| 6,638,980 B1 | | 10/2003 | Su et al. | |
| 6,790,866 B2 | | 9/2004 | Shuichi | |
| 2004/0082653 A1 | | 3/2002 | Shigeyuki | |

FOREIGN PATENT DOCUMENTS

| | | |
|---|---|---|
| CA | 2387107 | 3/2001 |
| DE | 199 47 457 A1 | 4/2001 |
| EP | 0491525 | 6/1992 |
| EP | 0686625 | 12/1995 |
| WO | WO94/15913 | 7/1994 |
| WO | 99/37607 | 7/1996 |
| WO | 96/25936 | 8/1996 |
| WO | WO 96/25936 | 8/1996 |
| WO | 98/04521 | 2/1998 |
| WO | WO 98/04521 | 2/1998 |
| WO | 98/18475 | 5/1998 |
| WO | WO 98/18475 | 5/1998 |
| WO | 98/18476 | 5/1998 |
| WO | WO 98/18476 | 5/1998 |
| WO | WO 99/37607 | 7/1999 |
| WO | WO 99/62891 | 12/1999 |
| WO | 00/12077 | 3/2000 |
| WO | WO 00/12077 | 3/2000 |
| WO | WO00/69465 | 11/2000 |
| WO | WO 00/78145 | * 12/2000 |
| WO | WO 01/29055 A2 | 4/2001 |
| WO | WO01/91558 | 12/2001 |

OTHER PUBLICATIONS

Ott et al., "Tetrahydroisoquino[2,1–d][1,4] Benzodiazepines. Synthesis and Neuropharmacological Activity," *Journal of Medicinal Chemistry* (American Chemical Society), 11: 777–787, 1968.
CAS Registry No. 380175–22–4 (2001).
CAS Registry No. 200404–31–5 (2000).
CAS Registry No. 380558–47–4 (2001).

(Continued)

*Primary Examiner*—Shailendra Kumar
(74) *Attorney, Agent, or Firm*—Ronald G. Ort

(57) ABSTRACT

The present invention is related to anthranilamides of formula I,

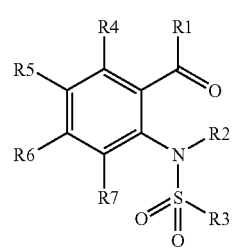

in which R(1) to R(7) have the meanings indicated herein, a process for their preparation, their use as medicaments, and pharmaceutical preparations containing them. The compounds act on the Kv1.5 potassium channel and inhibit a potassium current which is referred to as the ultra-rapidly activating delayed rectifier in the atrium of the human heart. The compounds are therefore suitable for use as novel antiarrhythmic agents for the treatment and prophylaxis of atrial arrhythmias (e.g., atrial fibrillation (AF) or atrial flutter).

24 Claims, No Drawings

OTHER PUBLICATIONS

CAS Registry No. 377769-29-4 (2001).
CAS Registry No. 378189-70-9 (2001).
CAS Registry No. 378225-17-3 (2001).
CAS Registry No. 377766-28-4 (2001).
CAS Registry No. 313375-86-9 (2001).
CAS Registry No. 377772-47-9 (2001).
CAS Registry No. 378192-06-4 (2001).
CAS Registry No. 378192-13-3 (2001).
CAS Registry No. 377766-36-4 (2001).
CAS Registry No. 377768-52-0 (2001).
CAS Registry No. 377769-97-6 (2001).
CAS Registry No. 377769-91-7 (2001).
CAS Registry No. 380169-27-7 (2001).
CAS Registry No. 377762-18-0 (2001).
CAS Registry No. 377762-27-1 (2001).
CAS Registry No. 377767-95-8 (2001).
CAS Registry No. 377769-25-0 (2001).
CAS Registry No. 377763-06-9 (2002).
CAS Registry No. 433702-31-9 (2002).
International Search Report for PCT/EP02/04138, mailed Sep. 23, 2002.
Amos, et al., Differences Between Outward Currents Of Human Atrial And Subepicardial Vehtricular Myocyles, J. Physiol., (1996), 491.1, 31–50.

Colatsky, et al., Potassium Channels As Targets For Antiarrhythmic Drug Action, Drug Dev. Res. (1990), 19:129–140.

Courtemanche, et al., Ionic Targets For Drug Therapy And Atrial Fibrillation–Induced Electrical Remodeling Insights From A Mathematical Model, Cardiovascular Research, (1999), 42:477–489.

Kakiuchi, et al., Non–peptide Inhibitors Of HCV Serine Proteinase, FEBS Letters (1998) 421, 217–220.

Li, et al., Evidence For Two Components Of Delayed Rectifier K+ Current In Human Ventricular Myocytes, Circ. Res., (1996), 78:689–696.

Nattel, Stanley, Newer Developments In The Management Of Atrial Fibrillation, Am. Heart J., (1995), 130:1094–1106.

Ott, et al., Tetrahydroisoquino[2,1–d][1,4]benzodiazepines. Synthesis and Neuropharmacological Activity, J. Med. Chem, (1998) 11:777–787.

Roden, Dan M., Current Status Of Class III Antiarrhythmic Drug Therapy, Am. J. Cardiol. (1993), 72:44B–49B.

Wang, et al., Sustained Depolarization–Induced Outward Current In Human Atrial Myocytes, Circ. Res., (1993) 73:1061–1076.

* cited by examiner

ANTHRANILAMIDES AND METHODS OF THEIR USE

The invention relates to compounds of formula I,

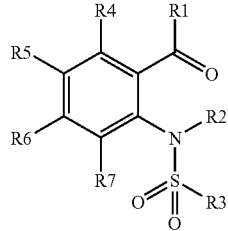

in which R(1), R(2), R(3), R(4), R(5), R(6) and R(7) have the meanings indicated hereinafter, to their preparation and use, and in particular, to their use as pharmaceuticals.

The compounds of formula I have not previously been disclosed. They act on the Kv1.5 potassium channel in the atrium of the human heart, which is referred to as ultra-rapidly activating delayed rectifier, and inhibit the potassium current. The compounds are therefore suitable as novel antiarrhythmic agents for the treatment and prophylaxis of atrial arrhythmias, e.g., atrial fibrillation (AF) or atrial flutter.

Atrial fibrillation (AF) and atrial flutter are the most common and persistent cardiac arrhythmias. Their occurrence increases with increasing age and frequently leads to other fatal symptoms, such as stroke. AF affects about 1 million Americans each year and leads to more than 80,000 strokes annually in the USA. The class I and III antiarrhythmic agents in use at present reduce the rate of AF occurrence, but can only be used in a limited manner due to their proarrhythmic side effects. Consequently, there is a great medical need to develop better medicaments for the treatment of atrial arrhythmias (S. Nattel (1995) "Newer developments in the management of atrial fibrillation," *Am. Heart J.*, 130:1094–1106).

It has been shown that most supraventricular arrhythmias are subject to reentry waves. Such reentry waves occur when the cardiac tissue exhibits slow conductivity and, at the same time, very short refractory periods. Increasing the myocardial refractory period by prolonging the action potential is an acknowledged mechanism for terminating arrhythmias and preventing development of arrhythmic conditions (T. J. Colatsky et al (1990), "Potassium channels as targets for antiarrhythmic drug action," *Drug Dev. Res.* 19:129–140). The length of the action potential is essentially determined by the extent of repolarizing K⁺ currents which flow out of the cells through various K⁺ channels. The delayed rectifier $I_K$, which consists of 3 different components, $IK_r$, $IK_s$ and $IK_{ur}$, plays an important role in this process.

Most of the known class III antiarrhythmics (e.g., dofetilide, E4031 and d-sotalol) predominantly or exclusively block the rapidly activating potassium channel $IK_r$, which can be detected both in cells of the human ventricle and in the atrium. However, it has emerged that these compounds increase the risk of arrhythmias at low or normal heart rates, in particular, arrhythmias referred to as torsades de pointes (D. M. Roden (1993) "Current status of class III antiarrhythmic drug therapy," *Am. J. Cardiol.* 72:44B–49B). In addition to this increased risk, which can be fatal, the efficacy of $I_{Kr}$ blockers declines at the lower heart rates experienced during conditions of tachycardia, precisely when the effective action of these blockers is needed most.

Whereas some of the disadvantages can possibly be overcome by blockers of the slowly activating component ($IK_s$), their efficacy has not yet been proven because no clinical investigations with $IK_s$ channel blockers are known.

The "ultra-rapidly" activating and very slowly deactivating component of the delayed rectifier is termed $IK_{ur}$ (=ultra-rapidly activating delayed rectifier). This corresponds to the Kv1.5 channel, and plays a major role in the repolarization time in the human atrium. Compared with the inhibition of $IK_r$ or $IK_s$, inhibition of the $IK_{ur}$ potassium outward current is a more effective method for lengthening the atrial action potential, thus terminating or preventing atrial arrhythmias. Mathematical models of human action potential suggest that the positive effects of blocking the $IK_{ur}$ should be particularly pronounced under the pathological conditions of chronic atrial fibrillation (M. Courtemanche, R. J. Ramirez, S. Nattel (1999) "Ionic targets for drug therapy and atrial fibrillation-induced electrical remodeling: insights from a mathematical model," *Cardiovascular Research*, 42:477–489).

In contrast to $IK_r$ and $IK_s$, which occur in the human ventricle, $IK_{ur}$ plays an important role in the human atrium but not the ventricle. Thus, unlike $IK_r$ and $IK_s$ blockers, the risk of a proarrhythmic effect from $IK_{ur}$ blockers in the ventricle is not a concern (Z. Wang et al (1993) "Sustained Depolarization-Induced Outward Current in Human Atrial Myocytes," *Circ. Res.*, 73:1061–1076; G. R. Li et al. (1996) "Evidence for Two Components of Delayed Rectifier K⁺-Current in Human Ventricular Myocytes," *Circ. Res.*, 78:689–696; G. J. Amos et al. (1996) "Differences between outward currents of human atrial and subepicardial ventricular myocytes," *J. Physiol.*, 491:31–50).

However, antiarrhythmic agents which act via selective blocking of the $IK_{ur}$ current or Kv1.5-channel have not been commercially available to date. Although a blocking effect on the Kv1.5 channel has been described for numerous pharmaceutical active substances (e.g., tedisamil, bupivacaine or sertindole), the Kv1.5 block here is only a side effect to the intended main effects of the substances.

WO 98 04 521 and WO 99 37 607 describe aminoindanes and aminotetrahydrona-phthalenes as potassium channel blockers which block the Kv1.5 channel. Structurally related aminochromanes are likewise described as Kv1.5 blockers in WO 00 12 077. In WO 99 62 891, thiazolidinones which block the potassium channel are also described. The applications WO 98 18 475 and WO 98 18 476 describe the use of various pyridazinones and phosphine oxides as antiarrhythmic agents which are said to act by blocking the $IK_{ur}$. However, the same compounds were known to be immunosuppressives (WO 96 25 936). All compounds described in these publications are completely different structurally from the presently disclosed compounds of the invention. Furthermore, the present inventors are not aware of any clinical data for the compounds disclosed in these publications. Since experience has shown that only a small proportion of active substances from preclinical research successfully overcome all clinical hurdles to gain approval as medicaments, there is still a need in the art for promising new compounds.

It has now been found, surprisingly, that the presently disclosed anthranilamides of formula I are potent blockers of the human Kv1.5 channel. These compounds can therefore be used as novel antiarrhythmics with a particularly advantageous safety profile. The compounds are particularly suitable for treating supraventricular arrhythmias, e.g., atrial fibrillation or atrial flutter.

The presently disclosed compounds can be employed for terminating existing atrial fibrillation or flutter in order to restore sinus rhythm (cardioversion). In addition, the substances reduce the susceptibility to recurrence of further fibrillation events (e.g., retention of sinus rhythm, prophylaxis).

The compounds of the invention have not previously been disclosed. Some structurally related compounds are described in the publications discussed hereinafter.

For example, compounds A and B, infra, were described in *FEBS Letters* (1981) 421:217–220, as serine protease inhibitors. Compounds C and D, infra, and similar derivatives, were described in *J. Med. Chem.* (1968) 11:777–787, as precursors for the synthesis of tetrahydroisoquino[2,1-d][1,4]benzodiazepines.

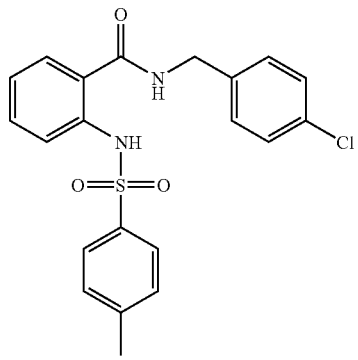

A

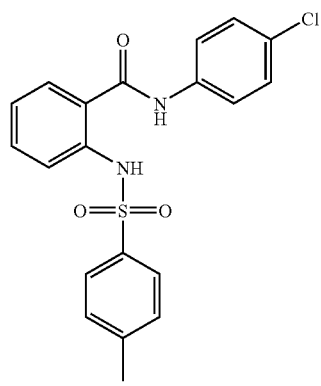

B

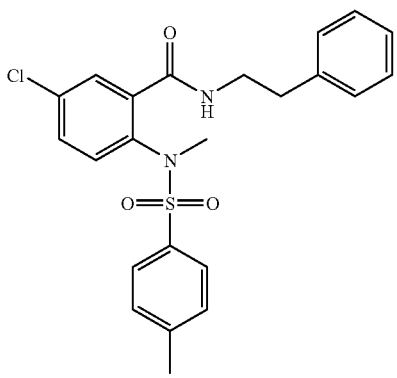

C

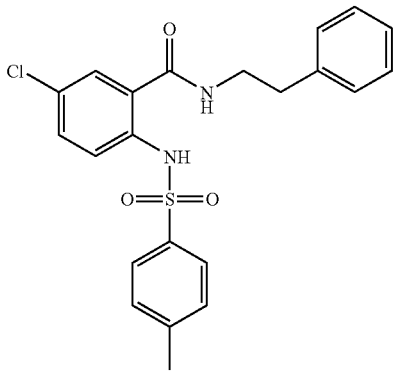

D

EP-A-686 625 describes anthranilic acid derivatives and their use as cGMP phosphodiesterase inhibitors. Most of the 144 compounds described in this reference contain carbonyl groups, which differ from the sulfonyl groups in the presently disclosed compounds. Three of the examples provide a sulfonylamino substituent (see, e.g., Example 131 in EP 686 625), which is structurally similar to compound E, infra. However, the reference provides no teaching or suggestion that such compounds function as phosphodiesterase inhibitors or that they may be used as antiarrhythmic agents.

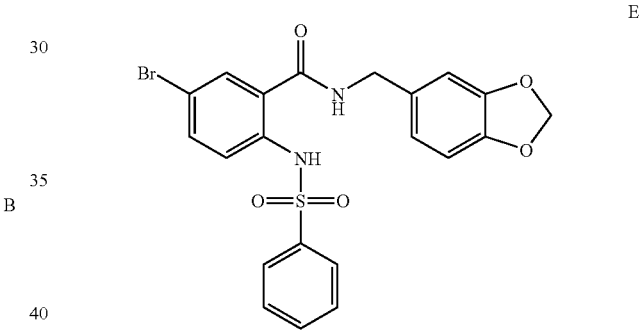

E

EP-A-947 500 claims a large, heterogeneous group of compounds which reportedly act as prostaglandin E2 antagonists or agonists. Most of the described anthranilic acid derivatives contain a free carboxylic acid function, thus differing from the presently disclosed compounds.

European patent application EP-A 0 491 525 describes anthranilamides with various 5-membered heterocycles in the side chain, such as compound F, for treating diabetes.

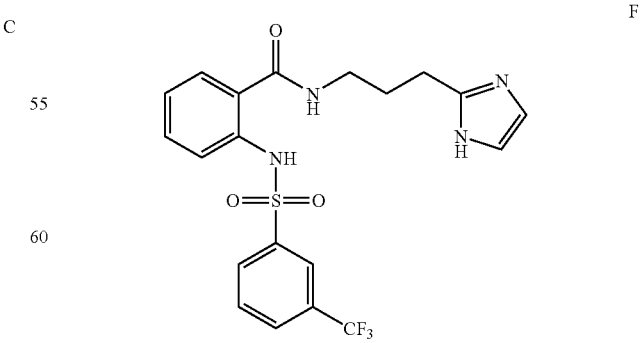

F

These publications, however, provide no teaching or suggestion that the disclosed compounds have a $K^+$-channelblocking action and may be useful as medicaments for the therapy and prophylaxis of K⁺-channel-mediated diseases, such as arrhythmia.

The present invention relates to compounds of formula I, $$\text{(I)}$$

in which:

R(1) is

A is —$C_nH_{2n}$—;
n is 0, 1, 2, 3, 4 or 5;
O is oxygen;
D is a bond or oxygen;
E is —$C_mH_{2m}$—;
m is 0, 1, 2, 3, 4 or 5;
R(8) is hydrogen, alkyl having 1, 2, 3 or 4 carbon atoms or $C_pH_{2p}$—R(14);
p is 0, 1, 2, 3, 4 or 5;
R(14) is cycloalkyl having 3, 4, 5 or 6 carbon atoms, aryl or heteroaryl,
where aryl and heteroaryl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(9) is hydrogen or alkyl having 1, 2, 3, 4, 5 or 6 carbon atoms;
R(10) is hydrogen, alkyl having 1, 2, 3 or 4 carbon atoms, cycloalkyl having 3, 4, 5 or 6 carbon atoms, aryl or heteroaryl,
where aryl and heteroaryl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(11) is cycloalkyl having 3, 4, 5 or 6 carbon atoms, phenyl, naphthyl, thienyl, furyl, pyridyl, pyrazinyl, pyridazinyl or pyrimidyl,
where phenyl, naphthyl, thienyl, furyl, pyridyl, pyrazinyl, pyridazinyl and pyrimidyl are unsubstituted or substituted by 1, 2 or 3 substituents selected from the group consisting of F, Cl, Br, I, $CF_3$, $OCF_3$, $NO_2$, CN, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(12) is alkyl having 1, 2, 3 or 4 carbon atoms, cycloalkyl having 3, 4, 5 or 6 carbon atoms, aryl or heteroaryl,
where aryl and heteroaryl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(13) is $C_pH_{2p}$—R'(14);
p is 0, 1, 2, 3, 4 or 5;
R'(14) is cycloalkyl having 3, 4, 5 or 6 carbon atoms tetrahydrofuranyl, tetrahydropyranyl, aryl or heteroaryl,
where aryl and heteroaryl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(15) is cycloalkyl having 3, 4, 5, 6, 7 or 8 carbon atoms;
R(2) is hydrogen or alkyl having 1, 2, 3 or 4 carbon atoms;
R(3) is alkyl having 3, 4, 5, 6 or 7 carbon atoms, cycloalkyl having 3, 4, 5 or 6 carbon atoms, phenyl or naphthyl,
where phenyl or naphthyl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(4), R(5), R(6) and R(7)
are, independently of one another, selected from the group consisting of hydrogen, F, Cl, Br, I, $CF_3$, $OCF_3$, $OCHF_2$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
and the pharmaceutically acceptable salts thereof.

In one embodiment, compounds of formula I include those in which:

A is —$C_nH_{2n}$—;
n is 0, 1, 2, 3, 4 or 5;

O is oxygen;

D is a bond or oxygen;

E is —$C_mH_{2m}$—;
 m is 0, 1, 2, 3, 4 or 5;

R(8) is hydrogen, alkyl having 1, 2, 3 or 4 carbon atoms or $C_pH_{2p}$—R(14);
 p is 0, 1, 2, 3, 4 or 5;
  R(14) is cycloalkyl having 3, 4, 5 or 6 carbon atoms, aryl or heteroaryl,
   where aryl and heteroaryl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(9) is hydrogen or alkyl having 1, 2, 3, 4, 5 or 6 carbon atoms;

R(10) is hydrogen, alkyl having 1, 2, 3 or 4 carbon atoms, cycloalkyl having 3, 4, 5 or 6 carbon atoms, aryl or heteroaryl,
 where aryl and heteroaryl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(11) is cycloalkyl having 3, 4, 5 or 6 carbon atoms, phenyl or pyridyl,
 where phenyl and pyridyl are unsubstituted or substituted by 1, 2 or 3 substituents selected from the group consisting of F, Cl, Br, I, $CF_3$, $OCF_3$, $NO_2$, CN, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(12) is alkyl having 1, 2, 3 or 4 carbon atoms, cycloalkyl having 3, 4, 5 or 6 carbon atoms, aryl or heteroaryl,
 where aryl and heteroaryl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(13) is $C_pH_{2p}$—R'(14);
 p is 0, 1, 2, 3, 4 or 5;
  R'(14) is cycloalkyl having 3, 4, 5 or 6 carbon atoms, tetrahydropyranyl, tetrahydrofuranyl, aryl or heteroaryl, where aryl and heteroaryl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(2) is hydrogen or alkyl having 1, 2, 3 or 4 carbon atoms;

R(3) is alkyl having 3, 4 or 5 carbon atoms, phenyl,
 where phenyl is unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(4), R(5), R(6) and R(7)
 are, independently of one another, selected from the group consisting of hydrogen, F, Cl, Br, I, $CF_3$, $OCF_3$, $OCHF_2$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

and the pharmaceutically acceptable salts thereof.

In another embodiment, compounds of formula I include those in which:

R(1) is $$R8\text{-}N(R9)\text{-}A(R10)\text{-}O\text{-}E\text{-}R11,$$

$$R8\text{-}N(R9)\text{-}A(R12)\text{-}D\text{-}E\text{-}R11 \text{ or}$$

$$R13\text{-}N(R9)\text{-}A(R10)\text{-}D\text{-}E\text{-}R11$$

A is —$C_nH_{2n}$—;
 n is 0, 1, 2 or 3;

O is oxygen;

D is a bond or oxygen;

E is —$C_mH_{2m}$—;
 m is 0, 1, 2 or 3;

R(8) is hydrogen or alkyl having 1, 2, 3 or 4 carbon atoms;

R(9) is hydrogen or alkyl having 1, 2, 3, 4, 5 or 6 carbon atoms;

R(10) is hydrogen, alkyl having 1, 2, 3 or 4 carbon atoms or cycloalkyl having 3, 4 or 5 carbon atoms, R(11) is cycloalkyl having 3, 4, 5 or 6 carbon atoms, phenyl or pyridyl,
 where phenyl and pyridyl are unsubstituted or substituted by 1, 2 or 3 substituents selected from the group consisting of F, Cl, Br, $CF_3$, $OCF_3$, $NO_2$, CN, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(12) is alkyl having 1, 2, 3 or 4 carbon atoms, cycloalkyl having 3, 4 or 5 carbon atoms, aryl or heteroaryl,
 where aryl and heteroaryl are unsubstituted or substituted by 1, 2 or 3 substituents selected from the group consisting of F, Cl, Br, $CF_3$, $OCF_3$, $NO_2$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(13) is $C_pH_{2p}$—R'(14);
 p is 0, 1, 2, 3, 4 or 5;
  R'(14) is cycloalkyl having 3, 4, 5 or 6 carbon atoms, tetrahydrofuranyl, tetrahydropyranyl, aryl or heteroaryl,
   where aryl and heteroaryl are unsubstituted or substituted by 1, 2 or 3 substituents selected from the group consisting of F, Cl, Br, $CF_3$, $OCF_3$, $NO_2$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(2) is hydrogen or alkyl having 1 or 2 carbon atoms;

R(3) is alkyl having 3, 4 or 5 carbon atoms, phenyl, where phenyl is unsubstituted or substituted by 1, 2 or 3 substituents selected from the group consisting of F, Cl, Br, $CF_3$, $OCF_3$, $NO_2$, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(4), R(5), R(6) and R(7)
are, independently of one another, selected from the group consisting of hydrogen, F, Cl, Br, $CF_3$, $OCF_3$, $OCHF_2$, $NO_2$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
and the pharmaceutically acceptable salts thereof.

In yet another embodiment, compounds of formula I include those in which:

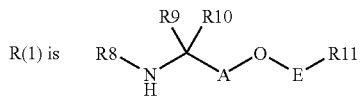

A is $—C_nH_{2n}—$;
n is 0, 1 or 2;
O is oxygen;
E is $—C_mH_{2m}—$;
m is 0 or 1;
R(8) is hydrogen or alkyl having 1, 2, 3 or 4 carbon atoms;
R(9) is hydrogen or alkyl having 1, 2, 3 or 4 carbon atoms;
R(10) is hydrogen or alkyl having 1 or 2 carbon atoms
R(11) is phenyl,
where phenyl is unsubstituted or substituted by 1, 2 or 3 substituents selected from the group consisting of F, Cl, $CF_3$, $OCF_3$, CN, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(2) is hydrogen;
R(3) is alkyl having 3, 4 or 5 carbon atoms, phenyl,
where phenyl is unsubstituted or substituted by 1, 2 or 3 substituents selected from the group consisting of F, Cl, $CF_3$, $OCF_3$, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(4), R(5), R(6) and R(7)
are, independently of one another, selected from the group consisting of hydrogen, F, Cl, $CF_3$, $OCF_3$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
and the pharmaceutically acceptable salts thereof.

In a further embodiment, compounds of formula I include those in which:

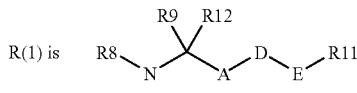

A is $—C_nH_{2n}—$;
n is 0, 1 or 2;
D is a bond or oxygen;
E is $—C_mH_{2m}—$;
m is 0 or 1;
R(8) is hydrogen or alkyl having 1, 2, 3 or 4 carbon atoms;
R(9) is hydrogen or alkyl having 1, 2, 3 or 4 carbon atoms;
R(11) is phenyl or pyridyl,
where phenyl and pyridyl are unsubstituted or substituted by 1, 2 or 3 substituents selected from the group consisting of F, Cl, $CF_3$, $OCF_3$, CN, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(12) is alkyl having 1, 2, 3 or 4 carbon atoms or cyclopropyl;
R(2) is hydrogen;
R(3) is alkyl having 3, 4 or 5 carbon atoms, phenyl,
where phenyl is unsubstituted or substituted by 1, 2 or 3 substituents selected from the group consisting of F, Cl, $CF_3$, $OCF_3$, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(4), R(5), R(6) and R(7)
are, independently of one another, selected from the group consisting of hydrogen, F, Cl, $CF_3$, $OCF_3$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
and the pharmaceutically acceptable salts thereof.

In another embodiment, compounds of formula I include those in which:

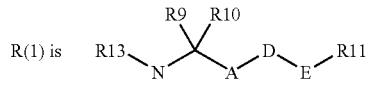

A is $—C_nH_{2n}—$;
n is 0, 1 or 2;
D is a bond or oxygen;
E is $—C_mH_{2m}—$;
m is 0 or 1;
R(9) is hydrogen or alkyl having 1 or 2 carbon atoms;
R(10) is hydrogen or alkyl having 1 or 2 carbon atoms;
R(11) is cycloalkyl having 3, 4, 5 or 6 carbon atoms, phenyl,
where phenyl is unsubstituted or substituted by 1, 2 or 3 substituents selected from the group consisting of F, Cl, $CF_3$, $OCF_3$, CN, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(13) is $C_pH_{2p}—R'(14)$;
p is 0, 1, 2, 3 or 4;
R'(14) is aryl or heteroaryl,
where aryl and heteroaryl are unsubstituted or substituted by 1, 2 or 3 substituents selected from the group consisting of F, Cl, $CF_3$, $OCF_3$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(2) is hydrogen;
R(3) is alkyl having 3, 4 or 5 carbon atoms, phenyl, where phenyl is unsubstituted or substituted by 1, 2 or 3 substituents selected from the group consisting of F, Cl, $CF_3$, $OCF_3$, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(4), R(5), R(6) and R(7)

are, independently of one another, selected from the group consisting of hydrogen, F, Cl, $CF_3$, $OCF_3$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

and the pharmaceutically acceptable salts thereof.

Alkyl radicals and alkylene radicals may be straight-chain or branched. This also applies to the alkylene radicals of formula $C_nH_{2n}$, $C_mH_{2m}$ and $C_pH_{2p}$. Alkyl radicals and alkylene radicals may also be straight-chain or branched if they are substituted or present in other radicals, e.g., in an alkoxy radical or in a fluorinated alkyl radical. Examples of alkyl radicals are methyl, ethyl, n-propyl, isopropyl, n-butyl, isobutyl, sec-butyl, tert-butyl, n-pentyl, isopentyl, neopentyl, n-hexyl, and 3,3-dimethylbutyl, heptyl. The divalent radicals derived from these radicals, e.g., methylene, 1,1-ethylene, 1,2-ethylene, 1,1-propylene, 1,2-propylene, 2,2-propylene, 1,3-propylene, 1,1-butylene, 1,4-butylene, 1,5-pentylene, 2,2-dimethyl-1,3-propylene, 1,6-hexylene, etc., are examples of alkylene radicals.

Cycloalkyl radicals may likewise be branched. Examples of cycloalkyl radicals having 3 to 7 carbon atoms are cyclopropyl, cyclobutyl, 1-methylcyclopropyl, 2-methylcyclopropyl, cyclopentyl, 2-methylcyclobutyl, 3-methylcyclobutyl, cyclopentyl, cyclohexyl, 2-methylcyclohexyl, 3-methylcyclohexyl, 4-methylcyclohexyl, cycloheptyl etc.

Suitable heteroaryl radicals include 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or 5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or 5-yl, 1,2,4-oxadiazol-3- or 5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or 5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7or 8-Isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, and 1-, 4-, 5-, 6-, 7- or 8-phthalazinyl. The corresponding N-oxides of these compounds are also included, for example, 2-, 3- or 4-pyridyl N-oxide.

Suitable heteroaromatic systems include thienyl, furyl, pyrrolyl, imidazolyl, quinolyl, pyrazolyl, pyridyl, pyrazinyl, pyrimidinyl and pyridazinyl.

Pyridyl refers to 2-, 3- and 4-pyridyl. Thienyl refers to both 2- and 3-thienyl. Furyl refers to both 2- and 3-furyl.

Aryl includes phenyl and 2- or 3-naphthyl.

Monosubstituted phenyl radicals may be substituted in the 2, 3 or 4 position, disubstituted in the 2,3, 2,4, 2,5, 2,6, 3,4 or 3,5 positions, or trisubstituted in the 2,3,4, 2,3,5, 2,3,6, 2,4,5, 2,4,6 or 3,4,5 positions. This also applies analogously to the N-containing heteroaromatic systems, the naphthyl, thienyl or furyl radical.

In the case of di- or trisubstitution of a radical, the substituents may be identical or different.

The compounds of formula I include those containing one or more acidic or basic groups or one or more basic heterocycles, and the corresponding physiologically or toxicologically tolerated salts, in particular the pharmaceutically usable salts. Compounds of formula I which carry acidic groups, e.g., one or more COOH groups, may be provided as alkali metal salts, such as sodium or potassium salts; alkaline earth metal salts, such as calcium or magnesium salts; or ammonium salts, such as salts with ammonia or organic amines or amino acids. For compounds of formula I in which R3 is hydrogen, for example, deprotonation of the sulfonamide moiety to yield a sodium salt is possible. Compounds of formula I which contain one or more basic (i.e., protonatable) groups or contain one or more basic heterocyclic rings can also be used in the form of their physiologically tolerated acid addition salts with inorganic or organic acids, such as hydrochlorides, phosphates, sulfates, methanesulfonates, acetates, lactates, maleates, fumarates, malates, gluconates, etc. If the compounds of formula I contain both an acidic and a basic group, the compounds may be provided as inert salts, e.g., betaines, in addition to the other salt forms described above. Salts can be obtained from the compounds of formula I by conventional processes, for example, by combination with an acid or base in a solvent or dispersant or by anion exchange from other salts.

With appropriate substitution, the compounds of formula I may be present in stereoisomeric forms. If the compounds of formula I contain one or more centers of asymmetry, they may, independently of one another, have the S-configuration or the R-configuration. The invention relates to the use of all possible stereoisomers (e.g., enantiomers or diastereomers), and mixtures of two or more stereomeric forms (e.g. enantiomers and/or diastereomers), in any desired ratio. The invention thus relates, for example, to enantiomers in enantiomerically pure form, both as levorotatory and as dextrorotatory antipodes, and also in the form of mixtures of the two enantiomers in different ratios or in the form of racemates. The preparation of individual stereoisomers can be effected, if desired, by separation of a mixture by conventional methods or, for example, by stereoselective synthesis. In the presence of one or more hydrogen atoms, the present invention also comprises all tautomeric forms of the compounds of formula I.

The compounds of formula I can be prepared by various chemical processes, some examples of which are outlined as scheme 1 or 2 below. The radicals R(1) to R(7) used herein are defined above.

According to scheme 1, below, compounds according to the invention can be prepared by first reacting an aminocarboxylic acid of formula 11, for example, with a sulfonyl chloride of formula R(4)—$SO_2$—Cl or a sulfonic acid anhydride, in a solvent such as water, pyridine or ether, in the presence of a base. Suitable bases include inorganic bases, such as sodium carbonate or potassium hydroxide; or organic bases, such as pyridine or triethylamine.

The resulting sulfonylaminocarboxylic acid of formula III can then be activated to give an acid chloride, for example, by reaction with a chlorinating agent such as phosphorus pentachloride, phosphorus oxychloride or thionyl chloride, in an inert solvent, followed by reaction with an amine of formula HR(1) to give the title compounds of formula I. The activation of the carboxylic acid group in the compound of formula III can also be effected by numerous methods familiar to a person skilled in the art, which are used in peptide chemistry for forming amide bonds; for example, by conversion to a mixed anhydride or an activated ester, or with the use of a carbodiimide, such as dicyclohexylcarbodiimide.

The reaction of the activated sulfonylamino carboxylic acid with an amine of formula H-R1 is typically carried out in an inert solvent such as pyridine, tetrahydrofuran or toluene with or without the addition of an inert base (for example, a tertiary amine or pyridine).

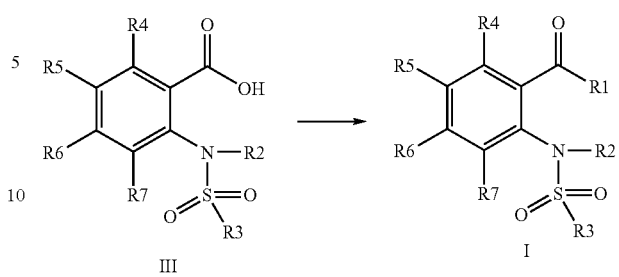

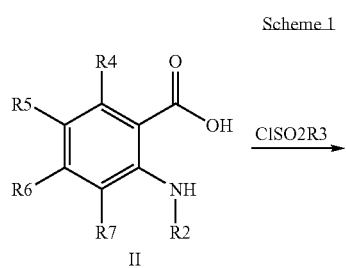

Alternatively, as shown in scheme 2 below, it is also possible to initially react the anhydrides of formula IV with an amine of formula H-R1 to give an o-aminobenzamide of formula VII; this aminobenzamide is then reacted with a sulfonyl chloride of formula $R(3)SO_2Cl$ to obtain a compound of formula I. Another possibility for preparing intermediates of formula VII in which R(2) is hydrogen comprises the amidation of an o-nitrobenzoic acid of formula V with an amine of formula HNR(1)R(2), followed by reduction of the nitro group to the amine.

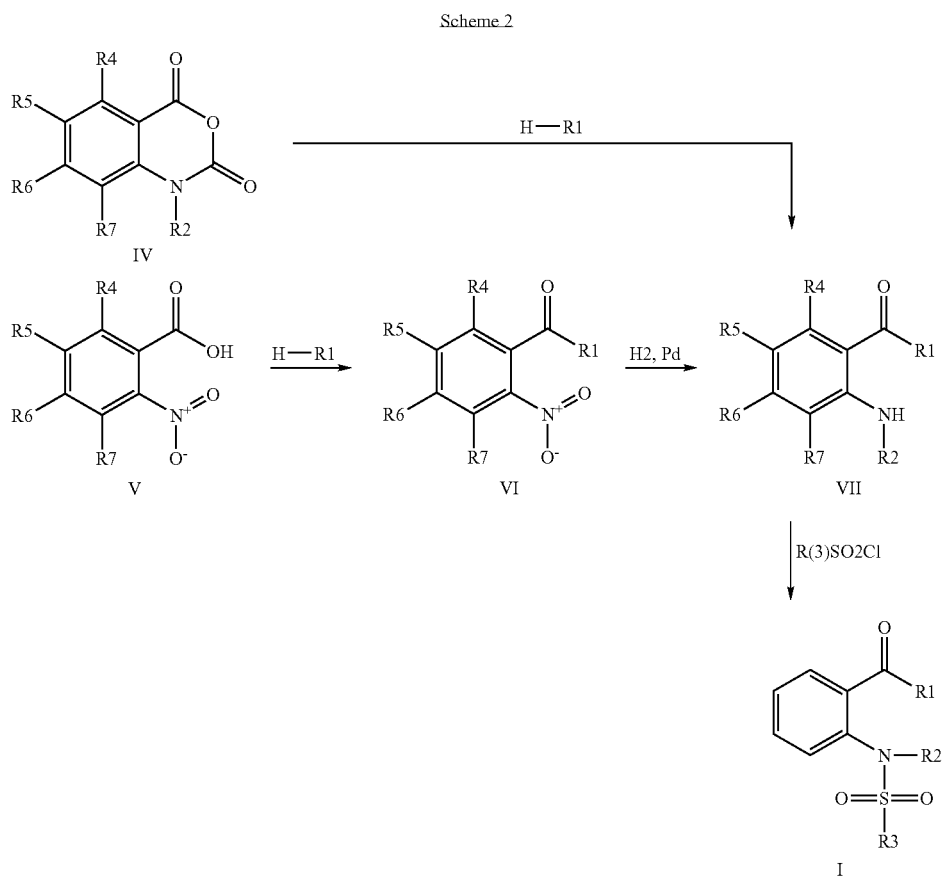

It may be appropriate in any of these procedures to temporarily protect functional groups in the molecule during certain reaction steps. Such protective group techniques are familiar to the skilled worker. The selection of a suitable protective group, and the processes for introducing and eliminating them, are described in the literature and can be adapted where appropriate to the individual compounds without difficulty.

The compounds of formula I and their physiologically tolerated salts can be used on animals, preferably on mammals and, in particular, on humans, as pharmaceuticals. Such pharmaceuticals may comprise an individual compound of formula I or mixtures of two or more such compounds in the form of pharmaceutical preparations. The present invention also relates to compounds of formula I and their physiologically tolerated salts for use as pharmaceuticals, to their use in the therapy and prophylaxis of the pathological states mentioned herein, and to their use for producing medicaments therefor and medicaments with $K^+$ channel-blocking effect. The present invention further relates to pharmaceutical preparations which comprise, as an active ingredient, an effective dose of at least one compound of formula I and/or a physiologically tolerated salt thereof. Such pharmaceutical preparations may further comprise conventional pharmaceutically acceptable carriers and excipients. The pharmaceutical preparations normally contain from 0.1 to 90% by weight of the compounds of formula I and/or their physiologically tolerated salts. The pharmaceutical preparations can be produced in a manner known in the art. For example, the compounds of formula I and/or their physiologically tolerated salts are mixed together with one or more solid or liquid pharmaceutical carriers and/or excipients and, if desired, with other active pharmaceutical ingredients, into a suitable administration form or dosage form. This dosage form may then be used as a pharmaceutical in human medicine or veterinary medicine.

Pharmaceuticals which comprise compounds of formula I and/or their physiologically tolerated salts can be administered orally, parenterally, intravenously, rectally, by inhalation or topically. The optimal administration will depend on the individual case, e.g., the particular manifestation of the disease to be treated.

Suitable pharmaceutically acceptable excipients are familiar to the skilled worker. Such excipients include solvents, gel formers, suppository bases, tablet excipients and other active ingredient carriers, for example, antioxidants, dispersants, emulsifiers, antifoams, flavor corrigents, preservatives, solubilizers, agents to achieve a depot effect, buffer substances or colorants.

The compounds of formula I can also be combined with other active pharmaceutical ingredients to achieve an advantageous therapeutic effect. Thus, in the treatment of cardiovascular disorders, combinations with substances acting on the cardiovascular system are possible and advantageous. Suitable combination partners of this type include, for example, class I, class II or class III antiarrhythmic agents, such as $IK_s$- or $IK_r$ channel blockers (e.g., dofetilide); antihypertensive substances, such as ACE inhibitors (e.g., enalapril, captopril, ramipril); angiotensin antagonists; $K^+$ channel activators; alpha- and beta-receptor blockers; sympathomimetic and adrenergic compounds; $Na^+/H^+$ exchange inhibitors; calcium channel antagonists; phosphodiesterase inhibitors; and other positively inotropic substances, such as digitalis glycosides or diuretics.

For oral use, the active compounds are mixed with additives suitable for this purpose, such as carriers, stabilizers or inert diluents, and converted by conventional methods into the suitable administration forms such as tablets, coated tablets, hard gelatin capsules, aqueous, alcoholic or oily solutions. Examples of inert carriers which can be used include gum arabic, magnesia, magnesium carbonate, potassium phosphate, lactose, glucose or starch, especially corn starch. Preparation is possible in this connection both as dry and as wet granules. Suitable oily carriers or solvents include, for example, vegetable or animal oils, such as sunflower oil or fish liver oil. Examples of suitable solvents for aqueous or alcoholic solutions include water, ethanol or sugar solutions or mixtures thereof. Further examples of excipients, also for other administration forms, are polyethylene glycols and polypropylene glycols.

For subcutaneous or intravenous administration, the active compounds are converted into a solution, suspension or emulsion, if desired, with the substances customary for this purpose such as solubilizers, emulsifiers or other excipients. The compounds of formula I and their physiologically tolerated salts can also be lyophilized and the resulting lyophilizates used, for example, to produce products for injection or infusion. Examples of suitable solvents include water, physiological saline or alcohols, e.g., ethanol, propanol, glycerol, as well as sugar solutions such as glucose or mannitol solutions, and mixtures of the various solvents mentioned.

Suitable pharmaceutical formulations for administration in the form of aerosols or sprays include, for example, solutions, suspensions or emulsions of the active ingredients of formula I, or their physiologically tolerated salts, in a pharmaceutically acceptable solvent such as ethanol or water, or a mixture of such solvents. The formulation can, if required, also contain other pharmaceutical excipients such as surfactants, emulsifiers and stabilizers, and a propellant gas. Such a preparation normally contains the active ingredient in a concentration of about 0.1 to 10, optionally about 0.3 to 3, percent by weight.

The dosage of the active ingredient of formula I to be administered or of the physiologically tolerated salt thereof typically depends on the individual case and should be adapted in a conventional way to the circumstances of the individual case for an optimal effect. Thus, the dose depends on the frequency of administration; the potency and duration of action of the compounds employed for therapy or prophylaxis; the nature and severity of the disease to be treated; the sex, age, weight and individual response of the human or animal to be treated; and whether the therapy is acute or prophylactic. The daily dose of a compound of formula I for a patient weighing about 75 kg is from 0.001 mg/kg of bodyweight to 100 mg/kg of bodyweight, optionally 0.01 mg/kg of bodyweight to 20 mg/kg of bodyweight. The dose can be administered in the form of a single dose or else be divided into a plurality of doses, e.g., two, three or four single doses. In the treatment of acute cases of cardiac arrhythmias, for example in an intensive care ward, parenteral administration by injection or infusion may also be advantageous, e.g., by a continuous intravenous infusion.

EXAMPLES

List of Abbreviations

DMAP 4-dimethylaminopyridine
DMF N,N-dimethylformamide
EDAC N-ethyl-N'-(3-dimethylaminopropyl)carbodiimide hydrochloride
EA ethyl acetate
HOBT 1-hydroxy-1H-benzotriazole
RT room temperature
THF tetrahydrofuran
BuLi butyllithium General Method 1: Reaction of Anthranilic Acids with Sulfonyl Chlorides to give o-sulfonylaminobenzoic Acids (Analogous to the Reaction Described in *Organic Syntheses* (1952), 32:8)

1.2 mol of the appropriate sulfonyl chloride were added in portions at 60° C. to a solution of 260 g (2.4 mol) of sodium carbonate and 1 mol of the appropriate anthranilic acid in 1.5 l of water. The reaction mixture was heated at 60–80° C. until the reaction was complete (about 1–6 h), adding further sulfonyl chloride, if necessary. After cooling, the reaction mixture was poured into 500 ml of 6 molar hydrochloric acid, and the precipitate was filtered off with suction and dried in vacuo in an oven at 45° C. If the product did not result as crystals, it was isolated by extraction with ethyl acetate.

Precursor 1 a: 2-(Toluene-4-sulfonylamino)benzoic acid

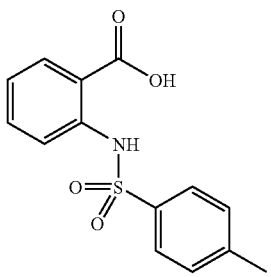

9.6 g of the title compound were obtained as a white solid from 6.85 g of anthranilic acid and 10.5 g of para-toluenesulfonyl chloride according to general method 1.

MS (ES): 293 (M+1).

Precursor 1 b: 2-Butylsulfonylamino-5-methylbenzoic acid

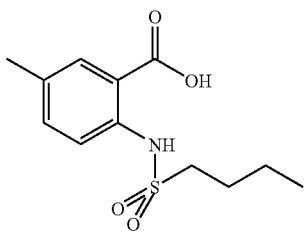

4.2 g of 2-butylsulfonylamino-5-methylbenzoic acid were obtained from 5 g of 5-methylanthranilic acid and 6.2 g of butanesulfonyl chloride according to general method 1.

MS (ES): 272 (M+1).

Precursor 1 c: 2-(4-Methoxybenzenesulfonylamino)-6-methylbenzoic acid

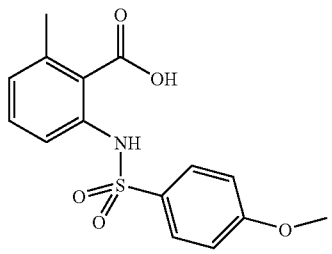

1.6 g of the title compound were obtained as a viscous oil from 1.5 g of 6-methylanthranilic acid and 2.3 g of 4-methoxybenzenesulfonyl chloride according to general method 1.

MS (ES): 323 (M+1).

The following further precursors were synthesized inter alia according to general method 1:

| Precursor | Structure | Mass (ES) |
| --- | --- | --- |
| 1 d | 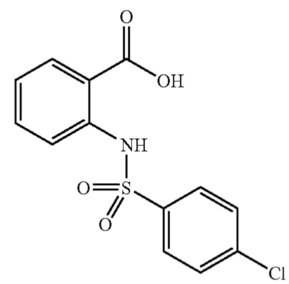 | 312 (M + 1) |
| 1 e | 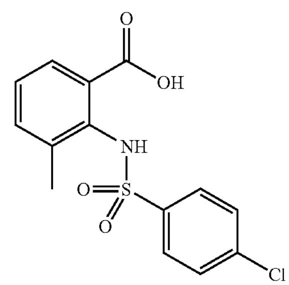 | 326 (M + 1) |
| 1 f | 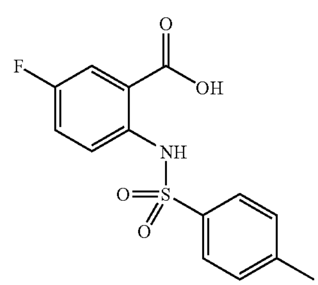 | 310 (M + 1) |
| 1 g | 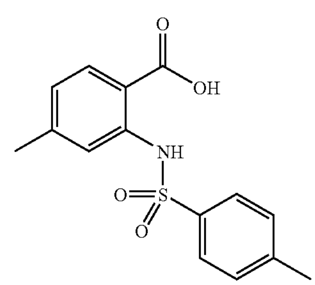 | 306 (M + 1) |
| 1 h | 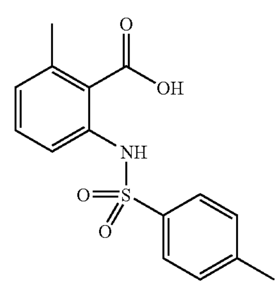 | 306 (M + 1) |

-continued

| Precursor | Structure | Mass (ES) |
|---|---|---|
| 1 i | 2-[(4-methoxyphenyl)sulfonylamino]benzoic acid | 308 (M + 1) |
| 1 j | 2-(phenylsulfonylamino)benzoic acid | 278 (M + 1) |
| 1 k | 2-[(4-chlorophenyl)sulfonylamino]-6-methylbenzoic acid | 326 (M + 1) |
| 1 l | 5-chloro-2-(phenylsulfonylamino)benzoic acid | 312 (M + 1) |
| 1 m | 5-chloro-2-[(4-methylphenyl)sulfonylamino]benzoic acid | 326 (M + 1) |
| 1 n | 5-methyl-2-(phenylsulfonylamino)benzoic acid | 292 (M + 1) |
| 1 o | 5-methoxy-2-[(4-methylphenyl)sulfonylamino]benzoic acid | 322 (M + 1) |
| 1 p | 5-methoxy-2-[[3-(trifluoromethyl)phenyl]sulfonylamino]benzoic acid | 376 (M + 1) |
| 1 q | 5-chloro-2-[(2-methoxy-4-methylphenyl)sulfonylamino]benzoic acid | 356 (M + 1) |
| 1 r | 2-[(3-methoxyphenyl)sulfonylamino]-3-methylbenzoic acid | 322 (M + 1) |
| 1 s | 2-[(3-methoxyphenyl)sulfonylamino]-4-methylbenzoic acid | 322 (M + 1) |

-continued

| Precursor | Structure | Mass (ES) |
|---|---|---|
| 1 t | 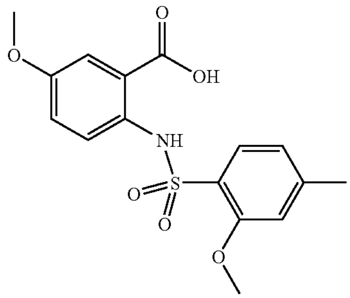 | 352 (M + 1) |
| 1 u | 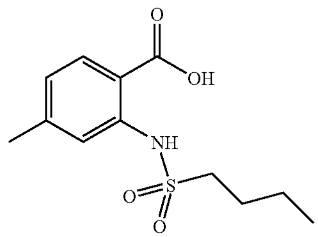 | 272 (M + 1) |

General method 2: Conversion of sulfonylaminobenzoic acids into the corresponding acid chlorides A) With Phosphorus Pentachloride 8 mmol of the sulfonylaminobenzoic acid were suspended in 15 ml of dry toluene and, at room temperature, 9.6 mmol of phosphorus pentachloride were slowly introduced. The mixture was stirred at 50° C. for 3 h, and cooled to 0° C., and the acid chloride was filtered off with suction, washed with a little toluene and dried in a vacuum oven at 45° C.

Precursor 2 a: 2-(4-Toluenesulfonylamino)benzoyl chloride

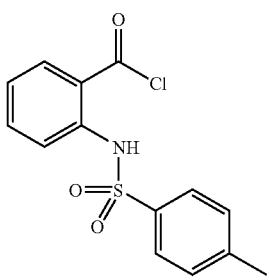

7.5 g of the title compound were isolated as white solid from 9.6 g of 2-(toluene-4-sulfonylamino)benzoic acid (precursor 1 a) and 8.3 g of phosphorus pentachloride.

MS (ES, detected as methyl ester after addition of methanol): 306 (M+1).

B) With Thionyl Chloride 8 mmol of the sulfonylaminobenzoic acid were heated in 6 ml of thionyl chloride at 60° C. for 3 h, and concentrated, and the residue was coevaporated twice with toluene.

Precursor 2 b: 2-(4-Methoxybenzenesulfonylamino)benzoyl chloride

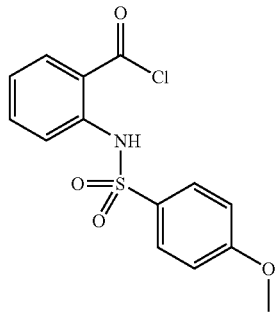

2.2 g of the title compound were obtained from 2.4 g of 2-(4-methoxybenzene-sulfonylamino)benzoic acid and 5 ml of thionyl chloride.

MS (ES, detected as methyl ester after addition of methanol): 322 (M+1).

The following further precursors were prepared inter alia according to general method 2 (variant A or B):

| Precursor | Structure | Mass (ES after addition of methanol to the acid chloride) Detection of the methyl esters |
|---|---|---|
| 2 c | 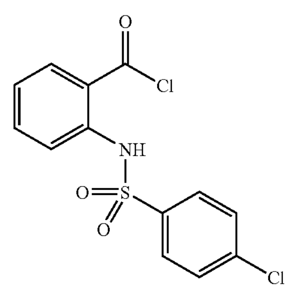 | 326 (M + 1) |
| 2 d | 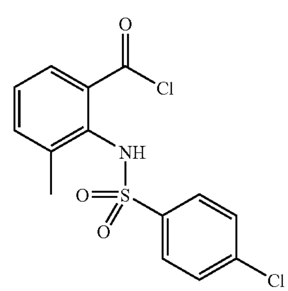 | 340 (M + 1) |
| 2 e | 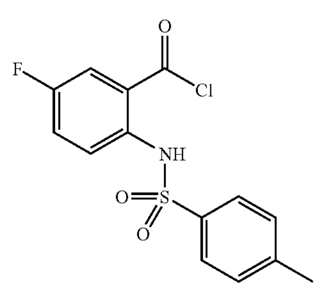 | 324 (M + 1) |

| Pre-cursor | Structure | Mass (ES after addition of methanol to the acid chloride) Detection of the methyl esters |
|---|---|---|
| 2 f | 4-methyl-2-(4-methylphenylsulfonamido)benzoyl chloride | 320 (M + 1) |
| 2 g | 3-methyl-2-(4-methylphenylsulfonamido)benzoyl chloride | 320 (M + 1) |
| 2 h | 2-(4-methoxyphenylsulfonamido)-3-methylbenzoyl chloride | 336 (M + 1) |
| 2 i | 2-(phenylsulfonamido)benzoyl chloride | 292 (M + 1) |
| 2 j | 2-(4-chlorophenylsulfonamido)-3-methylbenzoyl chloride | 340 (M + 1) |
| 2 k | 4-chloro-2-(phenylsulfonamido)benzoyl chloride | 326 (M + 1) |
| 2 l | 4-chloro-2-(4-methylphenylsulfonamido)benzoyl chloride | 340 (M + 1) |
| 2 m | 4-methyl-2-(phenylsulfonamido)benzoyl chloride | 306 (M + 1) |
| 2 n | 5-methoxy-2-(4-methylphenylsulfonamido)benzoyl chloride | 336 (M + 1) |
| 2 o | 5-methoxy-2-(3-(trifluoromethyl)phenylsulfonamido)benzoyl chloride | 390 (M + 1) |

| Precursor | Structure | Mass (ES after addition of methanol to the acid chloride) Detection of the methyl esters |
|---|---|---|
| 2 p | (4-chloro-2-{[(2-methoxy-4-methylphenyl)sulfonyl]amino}benzoyl chloride) | 370 (M + 1) |
| 2 q | (2-{[(3-methoxyphenyl)sulfonyl]amino}-3-methylbenzoyl chloride) | 336 (M + 1) |
| 2 r | (2-{[(3-methoxyphenyl)sulfonyl]amino}-4-methylbenzoyl chloride) | 336 (M + 1) |
| 2 s | (5-methoxy-2-{[(2-methoxy-4-methylphenyl)sulfonyl]amino}benzoyl chloride) | 366 (M + 1) |
| 2 t | (2-[(butylsulfonyl)amino]-4-methylbenzoyl chloride) | 286 (M + 1) |
| 2 u | (2-[(butylsulfonyl)amino]-5-methylbenzoyl chloride) | 286 (M + 1) |

General Method 3 A: Preparation of secondary amines by reductive amination 0.18 mmol of primary amine was dissolved in 200 ml of methanol and, after addition of 0.09 mol of aldehyde, 0.18 mmol of sodium cyanoborohydride and 0.18 mmol of glacial acetic acid, stirred at room temperature for 6 h. The solution was concentrated, taken up in ethyl acetate and washed twice with $NaHCO_3$ solution. The organic phase was concentrated, and the residue was distilled under high vacuum. In the case of involatile secondary amines, volatile constituents were distilled off and the residue was dissolved in ether/THF and, after addition of ethereal HCl solution, the precipitated hydrochloride was filtered off with suction, washed with ether and dried. The prepared secondary amines were employed without further purification for the reactions with the sulfonylaminobenzoyl chlorides or sulfonylaminobenzoic acids.

Precursor 3 a: Benzyl(1-methyl-1H-imidazol-2-ylmethyl)amine

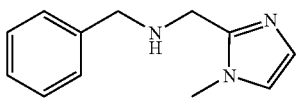

The hydrochloride (20.5 g) was prepared from 19.4 g of benzylamine and 10 g of 2-formyl-1-methylimidazole by the general procedure.

MS (ES+): m/z=202 (M+1).

Precursor 3 b: Benzylpyridin-3-ylmethylamine

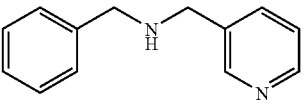

The secondary amine (2.8 g) was prepared by the general procedure from 4.32 g of 3-pyridylmethylamine and 2.12 g of benzaldehyde after Kugelrohr distillation under 0.1 mbar at 130° C.

MS (ES+): m/z=199 (M+1).

Precursor 3 c: Benzyl(3-imidazol-1-yl-propyl)amine

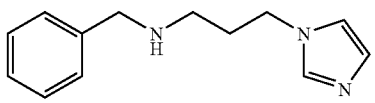

The secondary amine (3.5 g) was prepared by the general procedure from 12.5 g of 3-imidazol-1-ylpropylamine and 5.3 g of benzaldehyde after Kugelrohr distillation under 0.1 mbar at 130° C.

MS (ES+): m/z=216 (M+1).

The following further precursors were prepared inter alia by general procedure 3A:

| Precursor | Structure | Mass |
|---|---|---|
| 3 d | 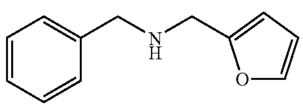 | 188 (M + 1) |
| 3 e | 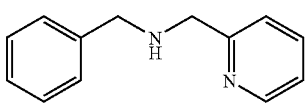 | 199 (M + 1) |
| 3 f | 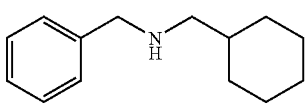 | 204 (M + 1) |
| 3 g | 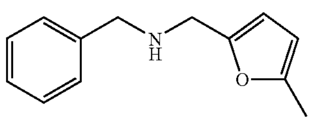 | 202 (M + 1) |
| 3 h | 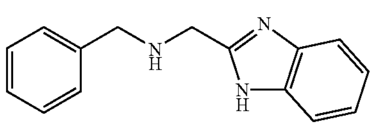 | 238 (M + 1) |
| 3 i | 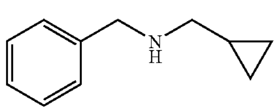 | 162 (M + 1) |
| 3 j | 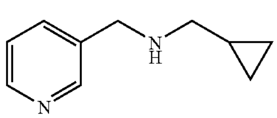 | 163 (M + 1) |
| 3 k | 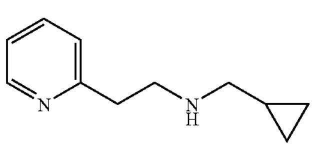 | 177 (M + 1) |
| 3 o | 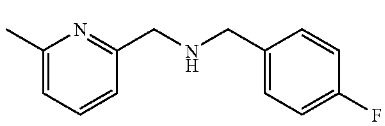 | 231 (M + 1) |
| 3 p | | 214 (M + 1) |
| 3 q | | 211 (M + 1) |
| 3 r | | 199 (M + 1) |

General Method 3 B: Preparation of α-branched amines from ketones

A solution of 67 mmol of the appropriate ketone in 120 ml of ethanol was added dropwise to a solution of 200 mmol of hydroxylammonium chloride and 200 ml of sodium acetate in 120 ml of water at 30° C., and the mixture was heated at 60° C. until reaction was complete (1–3 h). After cooling, the reaction mixture was diluted with water, and the precipitated oxide was filtered off with suction or, if necessary, isolated by extraction. The resulting product was dissolved in 100 ml of methanol, 100 ml of THF and 10 ml of concentrated ammonia solution and hydogenated in the presence of Raney nickel at RT under atmospheric pressure until hydrogen uptake ceased. Removal of the catalyst by filtration and concentration of the reaction mixture resulted in the corresponding amine which was purified by chromatography, if necessary.

Precursor 3 l: 1-Benzylpropylamine

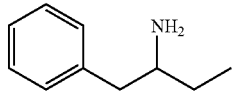

4.5 g of the title compound were obtained from 10 g of 1-phenyl-2-butanone according to general method 3.

Precursor 3 m: 1-Pyridin-4-ylpropylamine

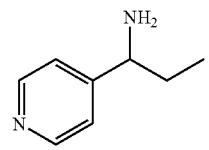

10.2 g of the title compound were obtained from 10 g of 4-propionylpyridine according to general method 3 B.

Precursor 3 n : 1-Pyridin-3-yl-propylamine

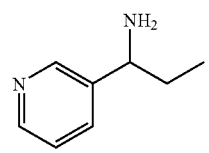

0.9 g of the title compound was obtained from 1 g of 3-propionylpyridine according to general method 3 B.

Precursor 3 s: 1-Cyclopropyl-1-phenylmethylamine hydrochloride

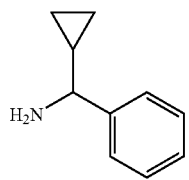

a) N-(Cyclopropylphenylmethyl)formamide 14.8 g (0.1 mol) of cyclopropyl phenyl ketone, 11.4 ml (0.3 mol) of formic acid and 20 ml (0.5 mol) of formamide were heated at 160° C. for 18 h. After cooling, 100 ml of water were added and the mixture was extracted 2× with 50 ml of ether each time. The ether phase was washed with 50 ml of 10% $Na_2CO_3$ solution, dried over $Na_2SO_4$ and concentrated. 13.6 g (77.4 mmol) of a yellow oil were obtained.

b) 1-Cyclopropyl-1-phenylmethylamine Hydrochloride 13.6 g (77.4 mmol) of N-(cyclopropylphenylmethyl) formamide (see a) were heated to reflux in 100 ml of 2N HCl for 18 h. After cooling, the mixture was extracted 2× with 50 ml of dichloromethane each time, and the aqueous phase was concentrated. The residue was taken up in 30 ml of 2-propanol, heated to boiling and cooled in a refrigerator overnight. The crystals of 1-cyclopropyl-1-phenylmethylamine hydrochloride which had separated out (3.85 g, 21 mmol) were filtered off with suction and dried in a vacuum oven.

Precursor 3 t: Cyclopropylpyridin-2-yl-methylamine hydrochloride

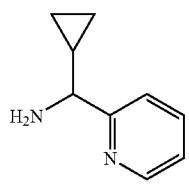

a) Cyclopropylpyridin-2-ylmethyleneamine 25 g (157.5 mmol) of 2-bromopyridine in 100 ml of diethyl ether were added dropwise over the course of 20 min to 100 ml (160 mmol) of n-BuLi solution in 300 ml of diethyl ether at −70° C. The dark red solution was stirred for 5 h and then 8.8 g (131 mmol) of cyclopropanecarbonitrile in 100 ml of ether were added. The mixture was stirred at −70° C. for 30 min, warmed to room temperature and stirred for a further 30 min. Then 15 g of $Na_2SO_4 \times 10H_2O$ were added, and stirring was continued for 1 h. The red solution was mixed with $Na_2SO_4$, filtered and concentrated. The product was distilled in a Kugelrohr apparatus at 75° C.–120° C./0.3 mbar as a pale yellow oil (18.6 g, 127 mmol) and was stored at −18° C.

b) Cyclopropylpyridin-2-ylmethylamine Hydrochloride 2.72 g (18.6 mmol) of cyclopropylpyridin-2-ylmethyleneamine (see a) were dissolved in 35 ml of dry methanol. At 0° C., 0.69 g (18.6 mmol) of $NaBH_4$ were added in portions. After 30 min at 0° C., the mixture was stirred at room temperature for 2 h and, after adjustment to pH 3 with 1 M HCl, the methanol was stripped off in a rotary evaporator and the residue was freeze-dried. 8.8 g of cyclopropylpyridin-2-ylmethylamine hydrochloride mixed with inorganic salts and boric acid were obtained.

Precursor 3 u: Cyclopropylpyridin-3-ylmethylamine hydrochloride

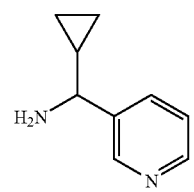

a) Cyclopropylpyridin-3-ylmethyleneamine 7.5 g (51 mmol) of the imine were isolated as a yellow oil in accordance with the method for precursor 3 p starting from 8.8 g (131 mmol) of cyclopropanecarbonitrile, 25 g (157.5 mmol) of 3-bromopyridine and 173 mmol of n-BuLi solution and after Kugelrohr distillation (130° C./0.2 mbar).

b) Cyclopropylpyridin-3-ylmethylamine Hydrochloride 16.6 g of cyclopropylpyridin-3-ylmethylamine hydrochloride mixed with inorganic salts and boric acid were obtained in accordance with the method for precursor 3 p starting from 7.5 g (51.5 mmol) of imine (see a) and 1.9 g (51.4 mmol) of $NaBH_4$.

Precursor 3 v: 1-(5-Methylfuran-2-yl)propylamine

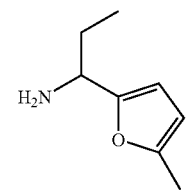

11.35 g (180 mmol) of sodium cyanoborohydride were introduced in portions into 5 g (36 mmol) of 2-methyl-5-propionylfuran and 28.2 g (366 mmol) of ammonium acetate in 300 ml of methanol with stirring and left to react at RT for 18 h. The mixture was substantially concentrated and, after addition of 200 ml of dichloromethane, the organic phase was washed 3× with 50 ml of $NaHCO_3$ solution each time, dried over $Na_2SO_4$ and concentrated. 3.9 g (28 mmol) of the amine were obtained in the form of a pale yellow oil.

Precursor 3 w: 1-Phenylprop-2-ynylamine hydrochloride

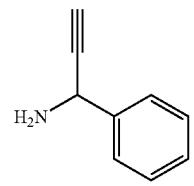

The compound was prepared in accordance with the method of Bjorn M. Nilsson et al., *J. Heterocycl. Chem.* (1989), 26(2):269–75, starting from 1-phenyl-2-propynyl alcohol by a Ritter reaction and subsequent hydrolysis with hydrochloric acid.

Precursor 3x: C-Cyclopropyl-C-(6-methoxypyridin-2-yl)methylamine

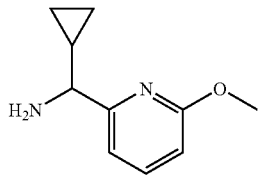

a) Cyclopropanecarbaldehyde O-benzyloxime 6.7 g (95.6 mmol) of cyclopropanecarbaldehyde were stirred together with 15.3 g (95.6 mmol) of O-benzylhydroxylamine and 15.7 g (191.2 mmol) of sodium acetate in 250 ml of ethanol at room temperature for 18 h and, after concentration, $Na_2SO_4$ was added. The residue was extracted 3× with 50 ml of dichloromethane each time, the organic phase was concentrated, and the crude product was purified by chromatography on silica gel. 5 g (28.6 mmol) of a colorless liquid were obtained.

b) O-Benzyl-N-[cyclopropyl-(6-methoxypyridin-2-yl)methyl]hydroxylamine 8.8 ml (22 mmol) of n-BuLi (2.5 M in toluene) were added to 3.76 g (20 mmol) of 2-bromo-6-methoxypyridine in 20 ml of THF at −78° C. After 30 min, this dark red solution was added to a solution of 1.4 g (8 mmol) of cyclopropanecarbaldehyde O-benzyloxime (see a) and 2.52 ml (20 mmol) of $BF_3$ etherate in 40 ml of toluene which had been stirred at −78° C. for 15 min. The mixture was stirred at −78° C. for 4 h, slowly warmed to RT and, after addition of water, made alkaline with saturated $Na_2CO_3$ solution.

The organic phase was separated off, the aqueous phase was extracted with toluene, and the combined organic phases were dried over $Na_2SO_4$ and concentrated. The crude product was taken up in 12 ml of acetonitrile, insolubles were removed, and the product was isolated by preparative HPLC (650 mg, red oil).

C-Cyclopropyl-C-(6-methoxypyridin-2-yl)methylamine 650 mg (2.3 mmol) of O-benzyl-N-[cyclopropyl-(6-methoxypyridin-2-yl)methyl]-hydroxylamine (see b) were dissolved in 18 ml of glacial acetic acid and diluted with 18 ml of water. 3.3 g of zinc dust were added, and the suspension was reacted in an ultrasonic bath for 24 h. The mixture was filtered, washed with 50% acetic acid, and the filtrate was partially evaporated and adjusted to pH 11 with saturated $Na_2CO_3$ solution. It was extracted 3× with 100 ml of dichloromethane each time, dried over $Na_2SO_4$ and concentrated. 0.4 g (2.2 mmol) of the product was obtained in the form of a dark red oil.

General Method 4 A: Preparation of 2-aminobenzamides from 2-nitrobenzoic acids

The appropriate 2-nitrobenzoic acid was initially reacted analogously to general methods 2 and 5 with the respective amine to give a 2-nitrobenzamide. Then 4 mmol of the 2-nitrobenzamide were hydrogenated in 50 ml of THF and 50 ml of methanol in the presence of a spatula tip of 10% palladium on carbon at RT under atmospheric pressure. The catalyst was filtered off with suction, the reaction mixture is concentrated, and the corresponding 2-aminobenzamide was obtained.

The following precursor was, inter alia, synthesized in this way:

| Precursor | Structure | Mass |
|---|---|---|
| 4 a | 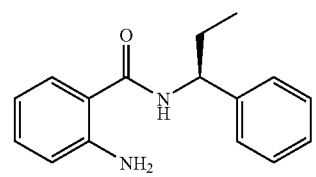 | 318 (M + 1) |

General Method 4 B: Preparation of 2-aminobenzamides from isatoic anhydride

A solution of 20 mmol of isatoic anhydride and 22 mmol of the appropriate amine in 75 ml of DMF was heated at 60° C. until reaction was complete. 100 ml of water were added to the reaction mixture, and the product was filtered off with suction or isolated by extraction.

Precursor 4 b: (S)-2-Amino-N-(1-phenylpropyl)benzamide 3.4 g of the title compound were obtained from 3 g of (S)-1-phenylpropylamine and 3.2 g of isatoic anhydride after 2 h at 60° C. in accordance with general method 4 B.

General method 5: Reaction of sulfonylaminobenzoyl chlorides with amines 0.6 mmol of the particular sulfonylaminobenzoyl chloride was added to a solution of 0.66 mmol of the particular amine and 0.9 mmol of triethylamine in 3 ml of methylene chloride, and the mixture was stirred at room temperature overnight. The reaction mixture was diluted with 5 ml of water and 10 ml of methylene chloride, and the organic phase was washed successively with 1 M hydrochloric acid solution and saturated sodium bicarbonate solution. After drying over magnesium sulfate, the solution was concentrated in vacuo, and the product was purified as necessary by preparative HPLC or column chromatography.

Example 1
(S)-2-Phenylsulfonylamino-5-chloro-N-(1-phenylethyl)benzamide

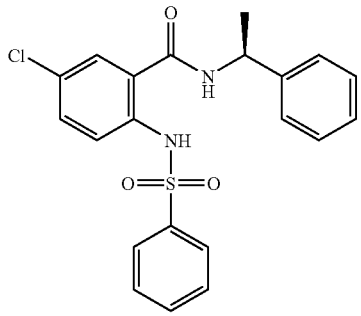

61 mg of the title compound were obtained from 2-phenylsulfonylamino-5-chlorobenzoyl chloride and S-(−)-1-methylbenzylamine in accordance with general method 5.
MS (ES+): m/z=415 (M+1).

Example 2
(R)-2-Phenylsulfonylamino-5-chloro-N-(1-phenylethyl)benzamide

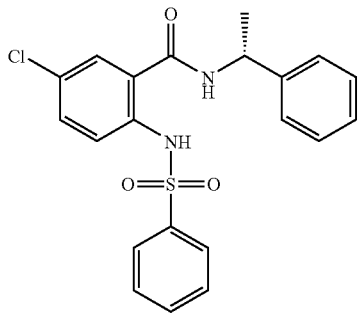

160 mg of the title compound were obtained from 2-phenylsulfonylamino-5-chlorobenzoyl chloride and R-(+)-1-methylbenzylamine in accordance with general method 5.
MS (ES+): m/z=415 (M+1).

Example 3
(S)-2-Phenylsulfonylamino-5-chloro-N-(1-phenylpropyl)benzamide

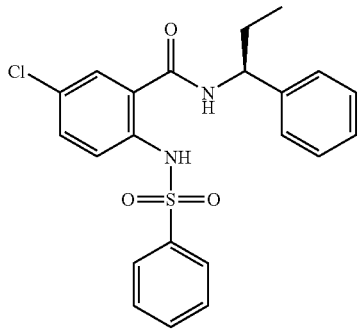

140 mg of the title compound were obtained from 2-phenylsulfonylamino-5-chlorobenzoyl chloride and S-(−)-1-ethylbenzylamine in accordance with general method 5.
MS (ES+): m/z=429 (M+1).

Example 4
(R)-2-Phenylsulfonylamino-5-chloro-N-(1-phenylpropyl)benzamide

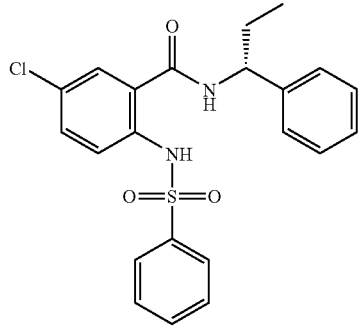

130 mg of the title compound were obtained from 2-phenylsulfonylamino-5-chlorobenzoyl chloride and R-(+)-1-ethylbenzylamine in accordance with general method 5.
MS (ES+): m/z=429 (M+1).

Example 5
(S)-2-Phenylsulfonylamino-5-chloro-N-[1-(4-methoxyphenyl)ethyl]-benzamide

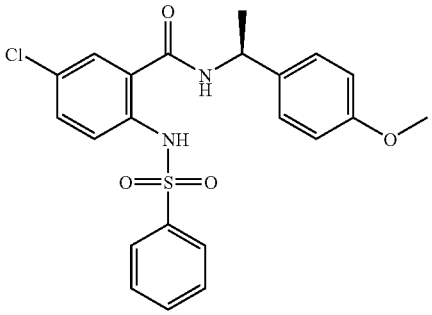

136 mg of the title compound were obtained from 2-phenylsulfonylamino-5-chlorobenzoyl chloride and S-(−)-1-(4-methoxyphenyl)ethylamine in accordance with general method 5.
MS (ES+): m/z=445 (M+1).

Example 6
(R)-2-Phenylsulfonylamino-5-chloro-N-[1-(4-methoxyphenylethyl]-benzamide

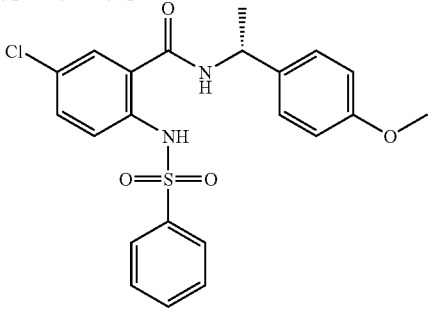

112 mg of the title compound were obtained from 2-phenylsulfonylamino-5-chlorobenzoyl chloride and R-(+)-1-(4-methoxyphenyl)ethylamine in accordance with general method 5.
MS (ES+): m/z=445 (M+1).

Example 7

2-Phenylsulfonylamino-5-chloro-N-(phenylpyridin-2-ylmethyl)benzamide

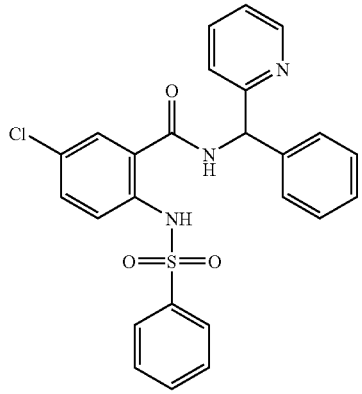

211 mg of the title compound were obtained from 2-phenylsulfonylamino-5-chlorobenzoyl chloride and C-phenyl-C-pyridin-2-ylmethylamine in accordance with general method 5.

MS (ES+): m/z=478 (M+1).

Example 8

N-Benzyl-N-pyridin-3-ylmethyl-2-(toluene-4-sulfonylamino)benzamide

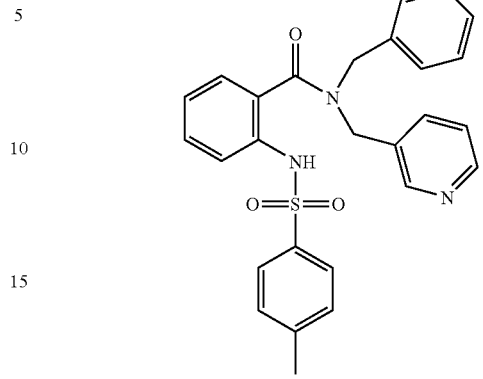

1.1 g of the title compound were obtained from 0.93 g of 2-para-toluenesulfonyl-aminobenzoyl chloride and 0.65 g of benzylpyridin-3-ylmethylamine (precursor 3b) in accordance with general method 5. The compound was isolated as a white salt after addition of ethereal HCl solution.

MS (ES+): m/z=472 (M+1).

The following further examples inter alia were prepared in accordance with general method 5:

| Example | Structure | Mass (ES) |
|---|---|---|
| 9 | 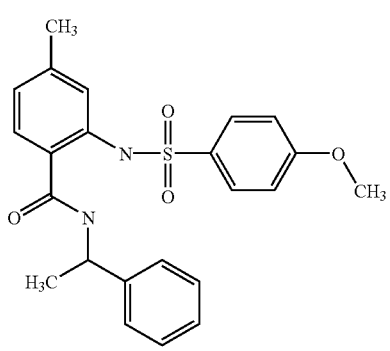 | 425 (M + 1) |
| 10 | 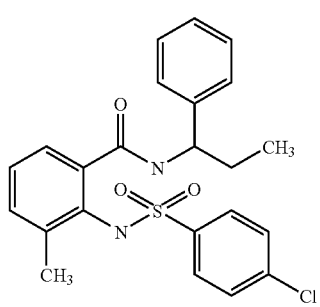 | 443 (M + 1) |

-continued
| Example | Structure | Mass (ES) |
|---|---|---|
| 11 | 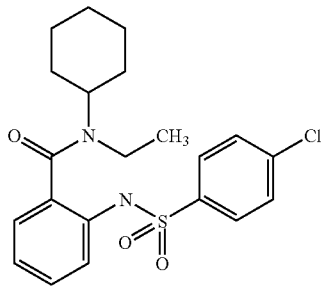 | 421 (M + 1) |
| 12 | 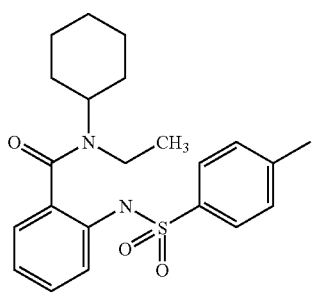 | 401 (M + 1) |
| 13 | 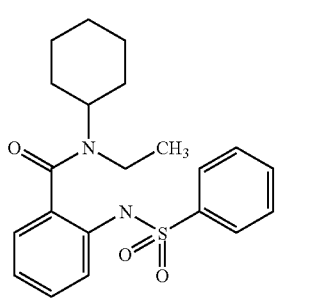 | 387 (M + 1) |
| 14 | 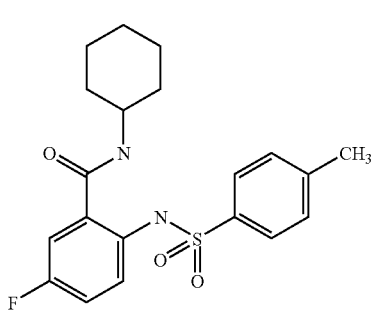 | 391 (M + 1) |
| 15 | 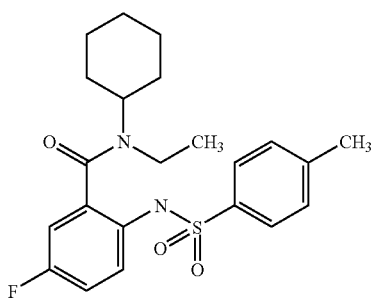 | 419 (M + 1) |

-continued
| Example | Structure | Mass (ES) |
|---|---|---|
| 16 | 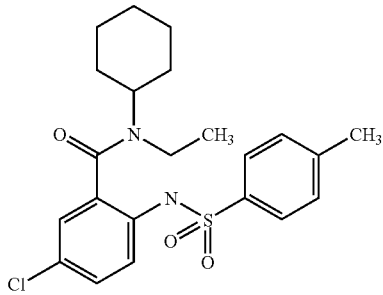 | 435 (M + 1) |
| 17 | 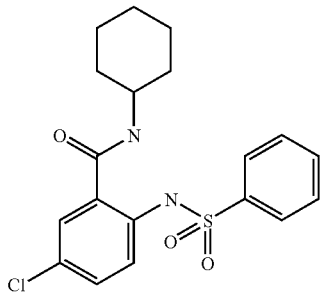 | 393 (M + 1) |
| 18 | 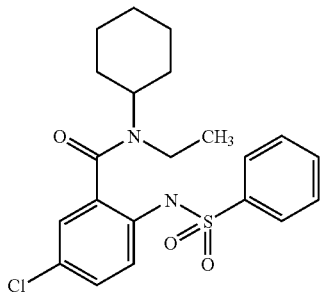 | 421 (M + 1) |
| 19 | 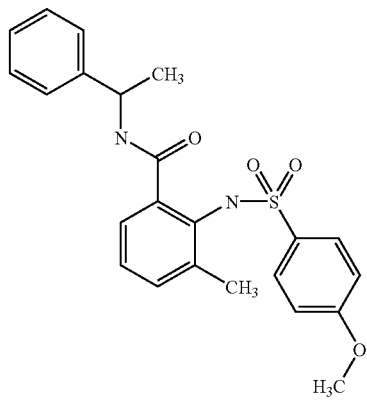 | 425 (M + 1) |
| 20 | 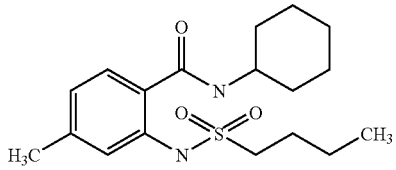 | 353 (M + 1) |

-continued
| Example | Structure | Mass (ES) |
|---|---|---|
| 21 | 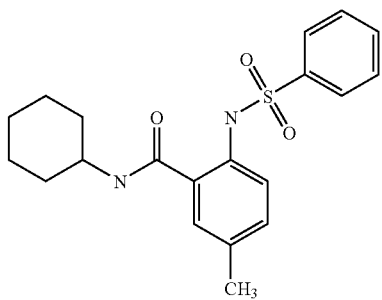 | 373 (M + 1) |
| 22 | 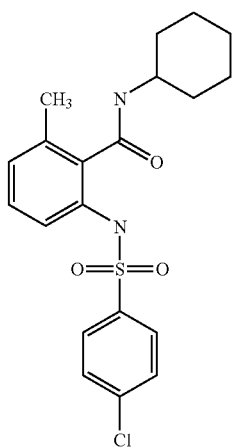 | 407 (M + 1) |
| 23 | 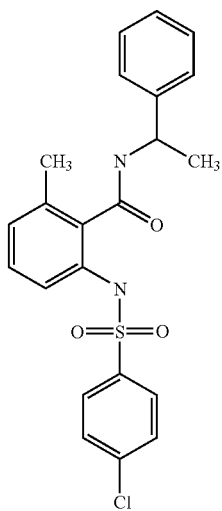 | 429 (M + 1) |

-continued

| Example | Structure | Mass (ES) |
|---|---|---|
| 24 | 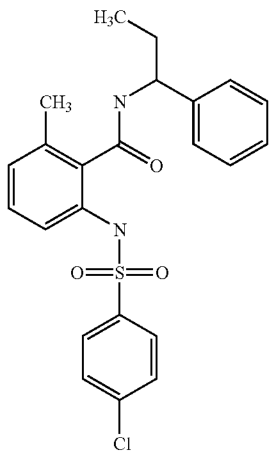 | 443 (M + 1) |
| 25 | 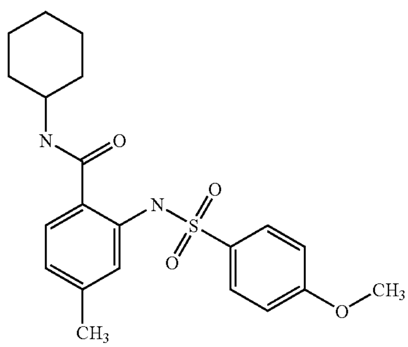 | 403 (M + 1) |
| 26 | 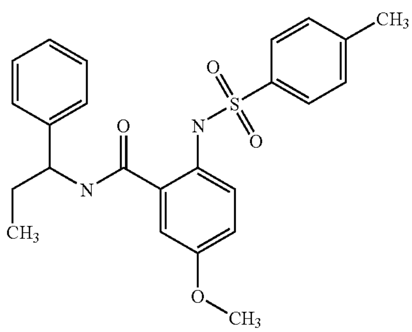 | 439 (M + 1) |
| 27 | 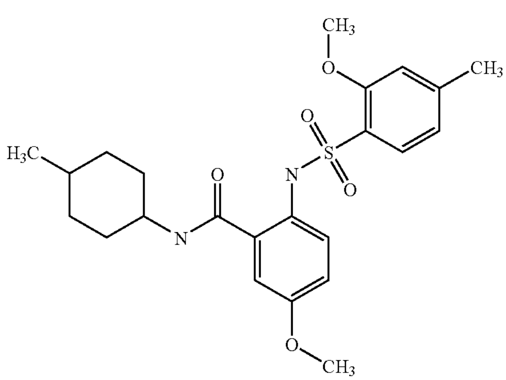 | 447 (M + 1) |

-continued

| Example | Structure | Mass (ES) |
|---------|-----------|-----------|
| 28 | 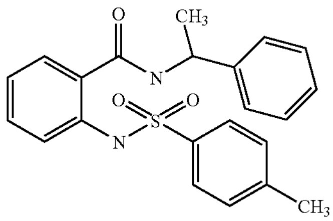 | 395 (M + 1) |
| 29 | 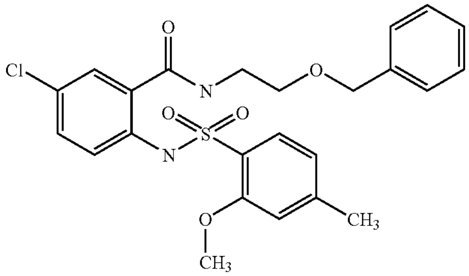 | 489 (M + 1) |
| 30 | 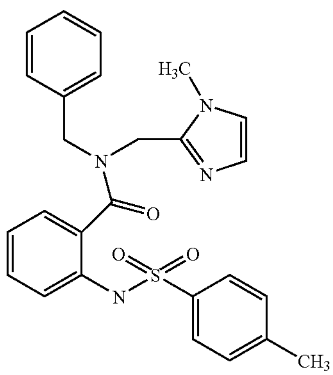 | 475 (M + 1) |
| 31 | 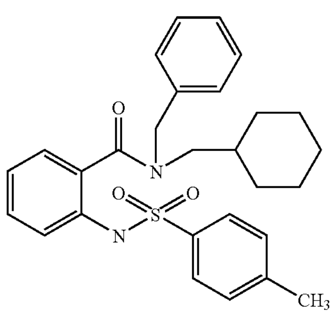 | 477 (M + 1) |
| 32 | 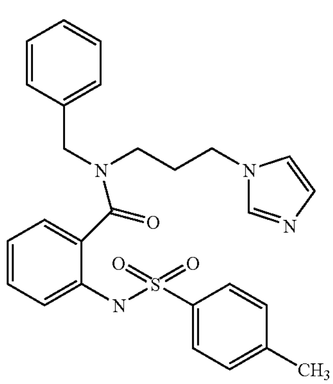 | 489 (M + 1) |

| Example | Structure | Mass (ES) |
|---|---|---|
| 33 | 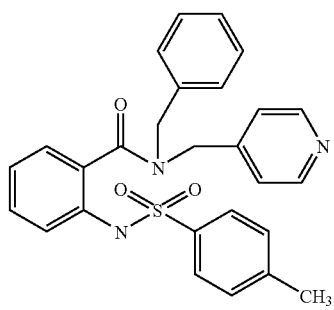 | 472 (M + 1) |
| 34 | 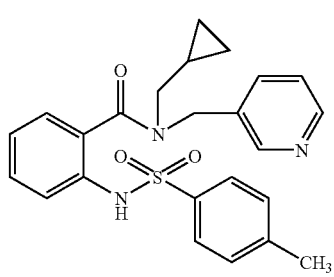 | 436 (M + 1) |
| 35 | 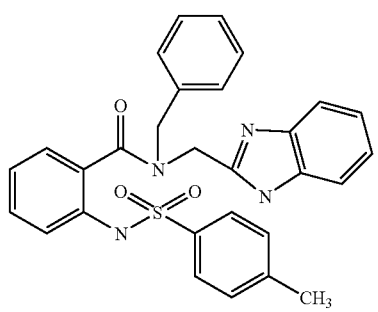 | 511 (M + 1) |
| 36 | 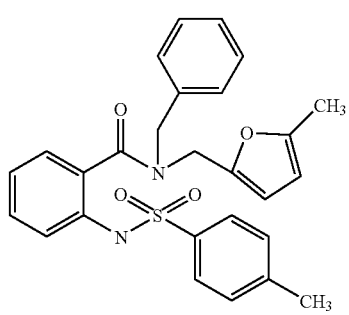 | 475 (M + 1) |
| 37 | 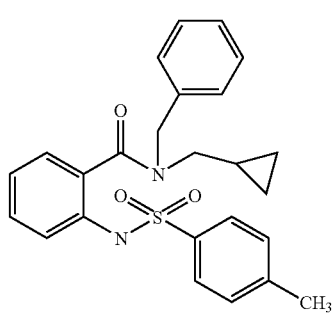 | 435 (M + 1) |

-continued
| Example | Structure | Mass (ES) |
|---|---|---|
| 38 | 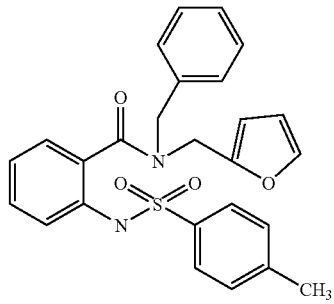 | 461 (M + 1) |
| 39 | 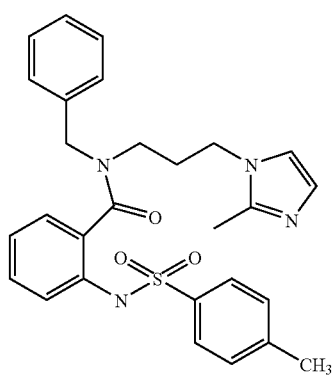 | 503 (M + 1) |
| 40 | 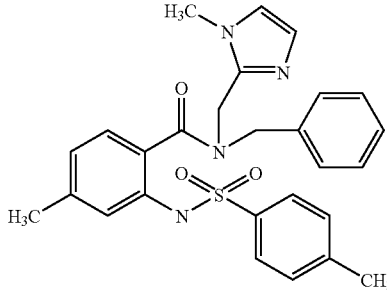 | 489 (M + 1) |
| 41 | 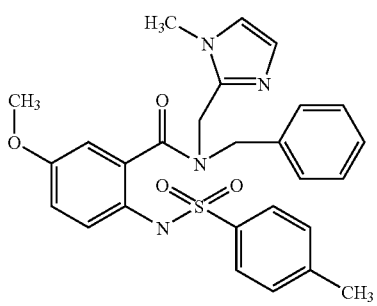 | 505 (M + 1) |
| 42 | 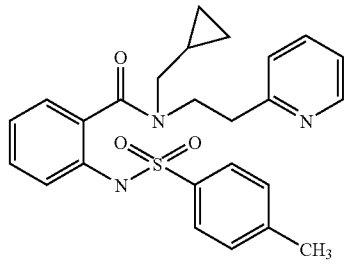 | 450 (M + 1) |

-continued
| Example | Structure | Mass (ES) |
|---------|-----------|-----------|
| 43 | 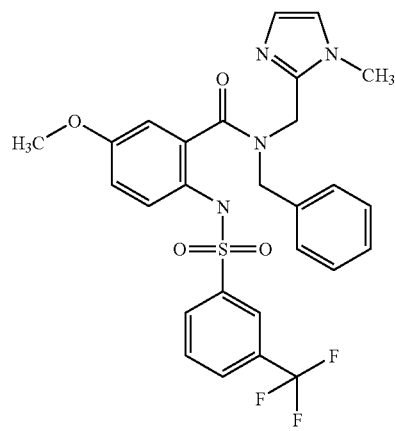 | 559 (M + 1) |
| 44 | 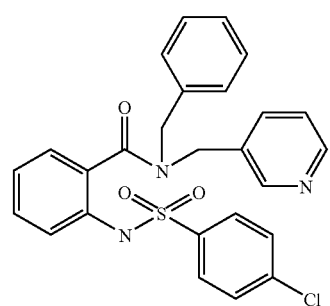 | 492 (M + 1) |
| 45 | 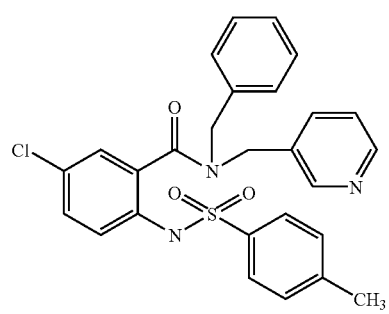 | 506 (M + 1) |
| 46 | 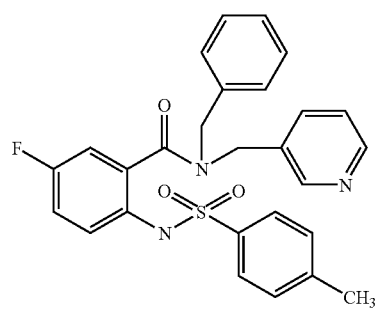 | 490 (M + 1) |

-continued

| Example | Structure | Mass (ES) |
|---------|-----------|-----------|
| 47 | 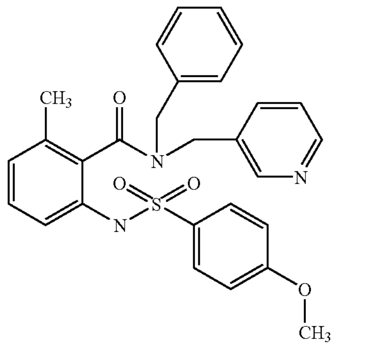 | 502 (M + 1) |
| 48 | 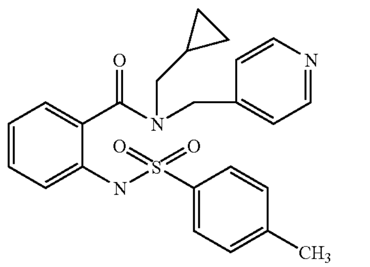 | 436 (M + 1) |
| 49 | 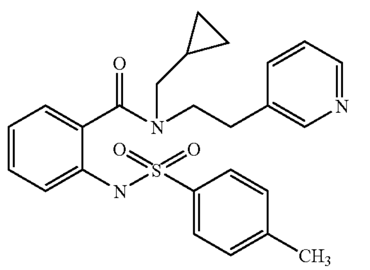 | 450 (M + 1) |
| 50 | 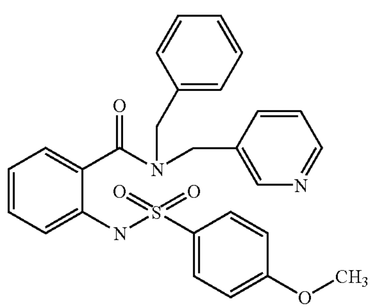 | 488 (M + 1) |
| 51 | 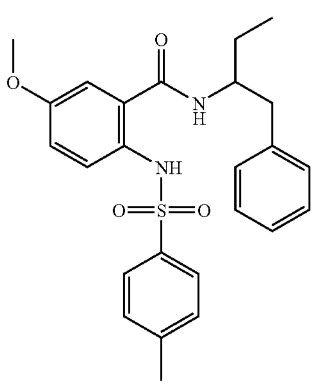 | 453 (M + 1) |

| Example | Structure | Mass (ES) |
|---|---|---|
| 52 | 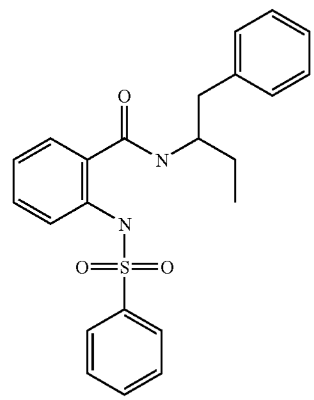 | 409 (M + 1) |
| 53 | 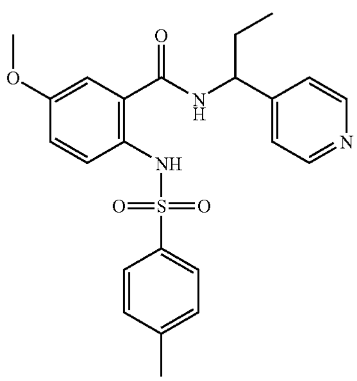 | 440 (M + 1) |

General Method 6: Reaction of sulfonylaminobenzoic acids with amines 0.44 mmol of the particular amine was added dropwise to a solution of 0.42 mmol of the appropriate sulfonylaminobenzoic acid, 0.44 mmol of HOBT and 0.44 mmol of EDAC in 5 ml of THF at 0° C., and the mixture was stirred at RT for 4 to 12 h. The reaction mixture was diluted with EA and washed with dilute hydrochloric acid and sodium bicarbonate solution. Drying over magnesium sulfate and concentrating in vacuo resulted in the appropriate amide which was purified as necessary by preparative HPLC.

Example 54

2-(Butylsulfonylamino)-N-cyclohexyl-5-methylbenzamide

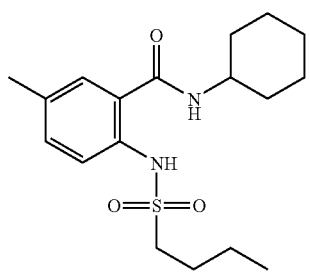

184 mg of the title compound were obtained from 200 mg of 2-butylsulfonylamino-5-methylbenzoic acid (precursor 1 b) and cyclohexylamine in accordance with general method 6.

MS (ES+): m/z 353 (M+1).

The following further examples inter alia were obtained in accordance with general method 6:

| Example | Structure | Mass |
|---|---|---|
| 55 | 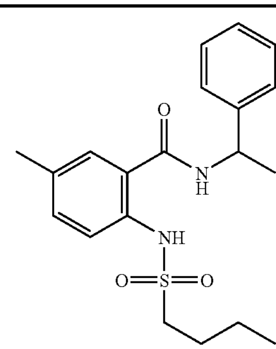 | 375 (M + 1) |

| Example | Structure | Mass |
|---|---|---|
| 56 | 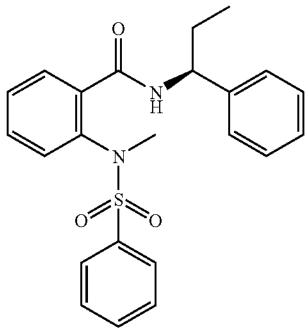 | 409 (M + 1) |
| 57 | 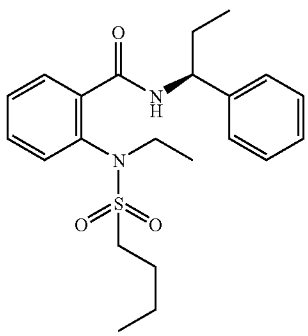 | 403 (M + 1) |
| 58 | 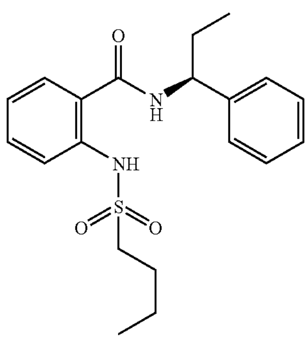 | 375 (M + 1) |

General Method 7: Reaction of 2-aminobenzamides with sulfonyl chlorides

A solution of 0.3 mmol of the appropriate sulfonyl chloride in 2 ml of methylene chloride was added dropwise to a solution of 0.2 mmol of the appropriate 2-aminobenzamide (precursor 4) and 0.6 mmol of pyridine in 5 ml of methylene chloride at 0° C., and the mixture was stirred at RT overnight. The organic phase was washed with water, dilute hydrochloric acid and sodium bicarbonate solution, and the resulting crude product was purified if necessary by preparative HPLC.

The following products inter alia were obtained in this way:

| Example | Structure | Mass |
|---|---|---|
| 59 | 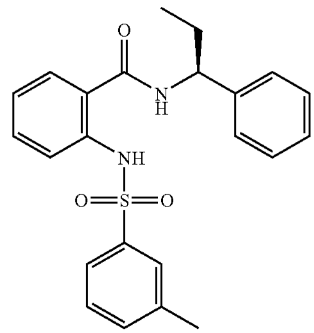 | 409 (M + 1) |
| 60 | 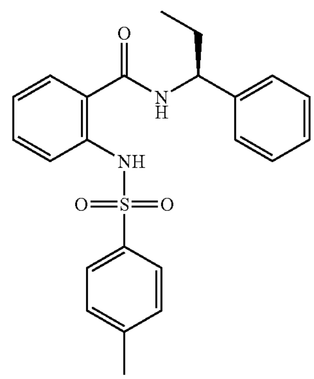 | 409 (M + 1) |
| 61 | 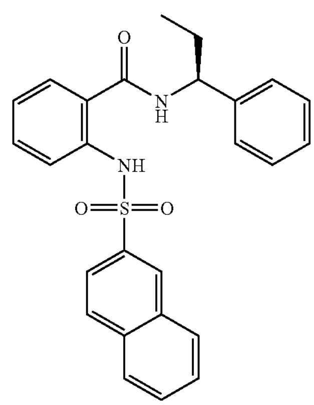 | 445 (M + 1) |
| 62 | 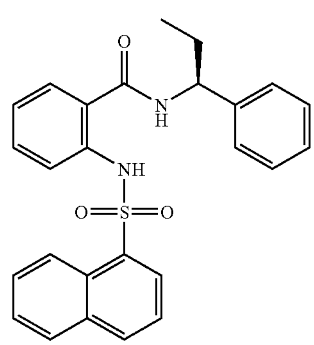 | 445 (M + 1) |

-continued

| Example | Structure | Mass |
|---------|-----------|------|
| 63 | 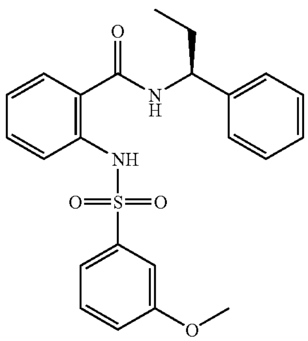 | 425 (M + 1) |
| 64 | 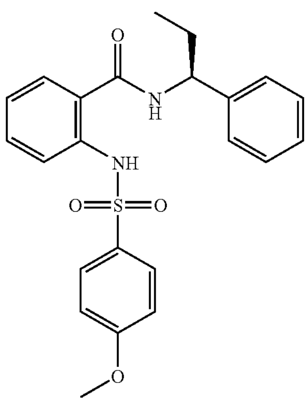 | 425 (M + 1) |
| 65 | 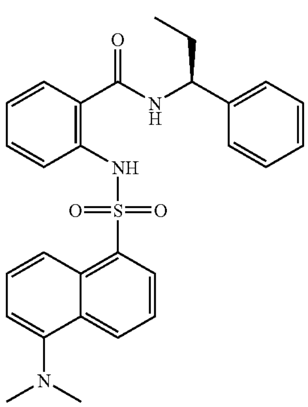 | 488 (M + 1) |
| 66 | 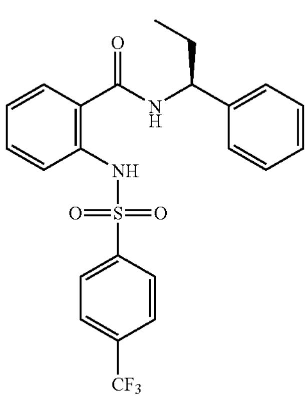 | 463 (M + 1) |

-continued

| Example | Structure | Mass |
|---------|-----------|------|
| 67 | 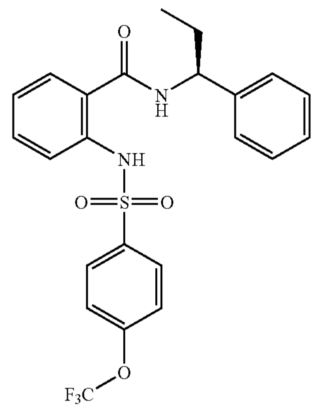 | 479 (M + 1) |
| 68 | 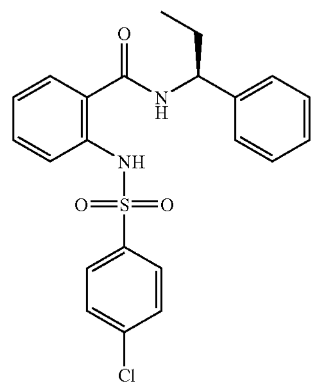 | 429 (M + 1) |
| 69 | 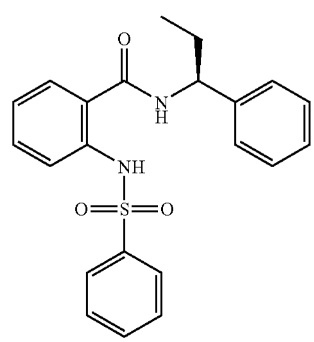 | 395 (M + 1) |
| 70 | 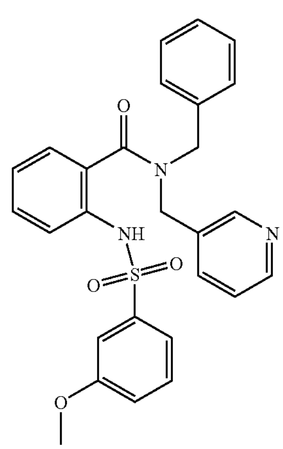 | 488 (M + 1) |

-continued

| Example | Structure | Mass |
|---------|-----------|------|
| 71 | 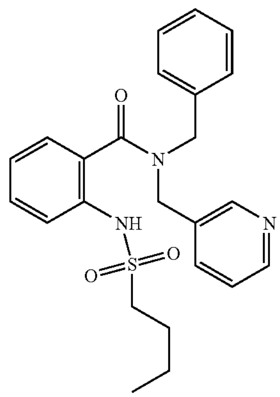 | 438 (M + 1) |
| 72 | 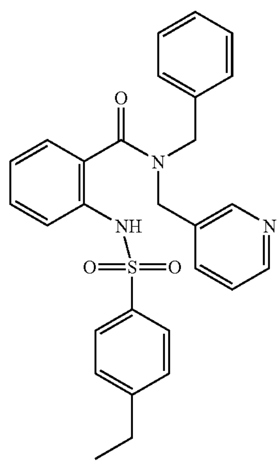 | 486 (M + 1) |
| 73 | 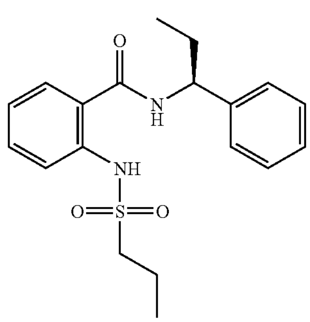 | 361 (M + 1) |
| 74 | 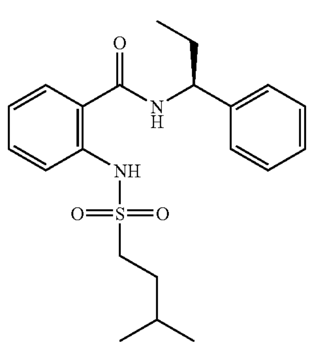 | 389 (M + 1) |

-continued

| Example | Structure | Mass |
|---------|-----------|------|
| 75 | 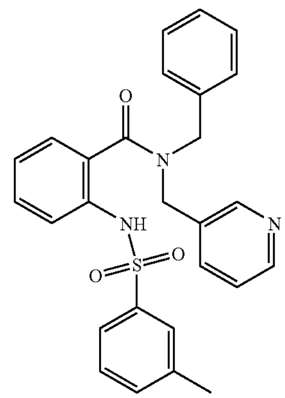 | 472 (M + 1) |
| 76 | 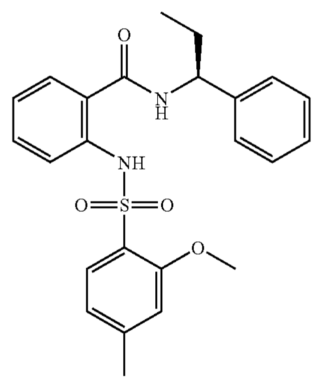 | 439 (M + 1) |
| 77 | 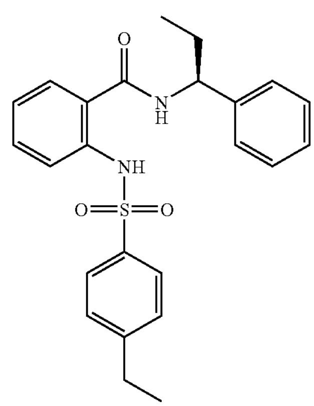 | 423 (M + 1) |

The 3-methylbutylsulfonyl chloride required for example 74 was prepared from 3-methylbutyl bromide by reaction with ammonium sulfite solution under reflux to give the sulfonic acid, followed by chlorination with phosphorus pentachloride to give the sulfonyl chloride.

The following compounds were additionally obtained analogously to the above examples and by use of one or more of general methods 1–7:

| Example | Structure | Mass |
|---|---|---|
| 78 | 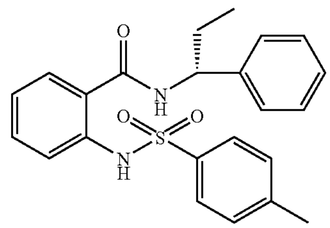 | 409 (M + 1) |
| 79 | 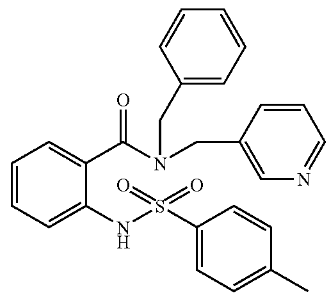 | 472 (M + 1) |
| 80 | 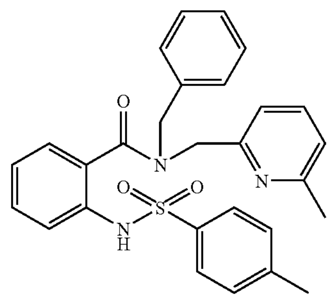 | 485 (M + 1) |
| 81 | 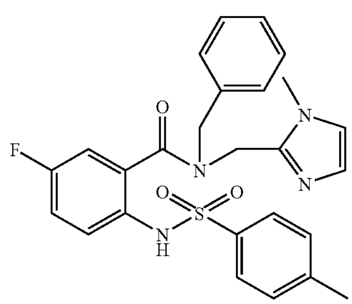 | 493 (M + 1) |
| 82 | 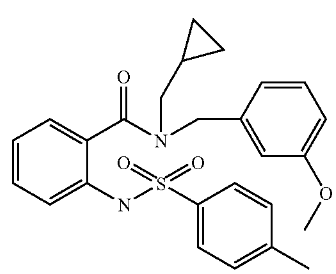 | 465 (M + 1) |
| 83 | | 474 (M + 1) |
| 84 | | 478 (M + 1) |
| 85 | | 425 (M + 1) |
| 86 | | 460 (M + 1) |
| 87 | | 486 (M + 1) |

| Example | Structure | Mass |
|---|---|---|
| 88 | 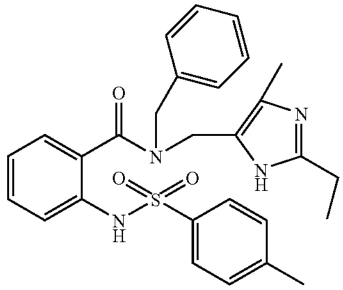 | 503 (M + 1) |
| 89 | 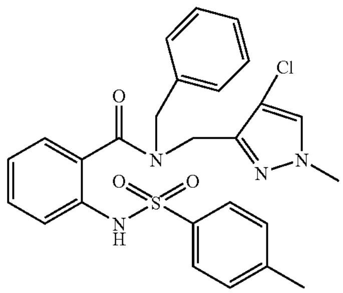 | 509 (M + 1) |
| 90 | 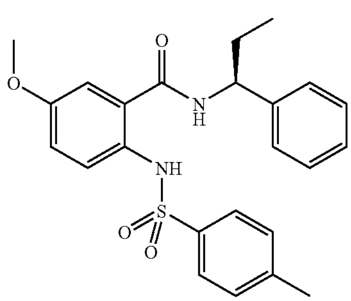 | 439 (M + 1) |
| 91 | 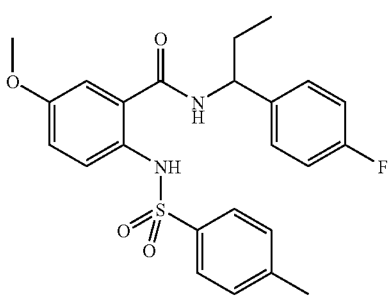 | 457 (M + 1) |
| 92 | 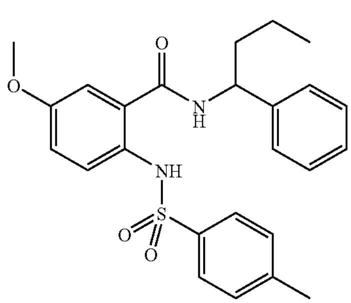 | 453 (M + 1) |
| 93 | | 451 (M + 1) |
| 94 | | 407 (M + 1) |
| 95 | | 431 (M + 1) |
| 96 | | 455 (M + 1) |

-continued
| Example | Structure | Mass |
|---|---|---|
| 97 | 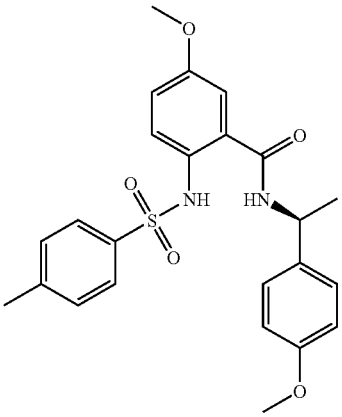 | 455 (M + 1) |
| 98 | 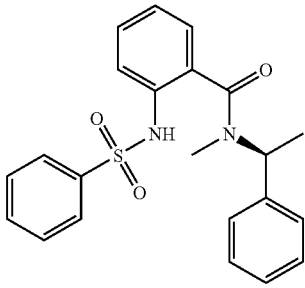 | 395 (M + 1) |
| 99 | 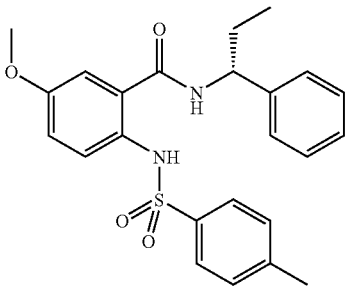 | 439 (M + 1) |
| 100 | 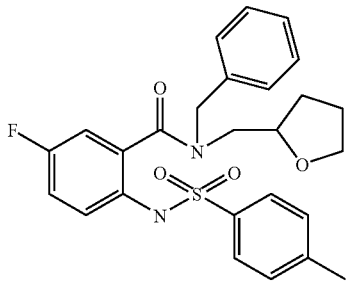 | 483 (M + 1) |
-continued
| Example | Structure | Mass |
|---|---|---|
| 101 | 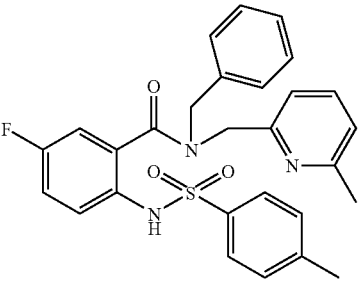 | 504 (M + 1) |
| 102 | 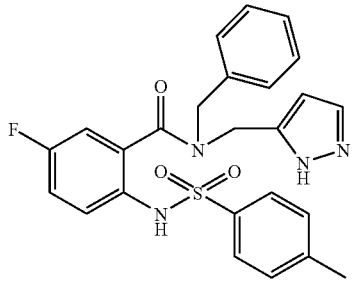 | 479 (M + 1) |
| 103 | 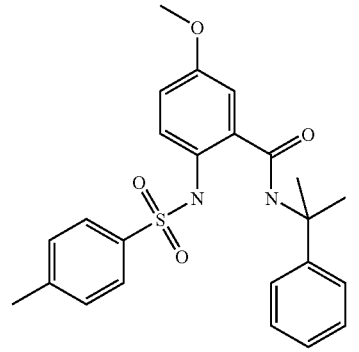 | 439 (M + 1) |
| 104 | 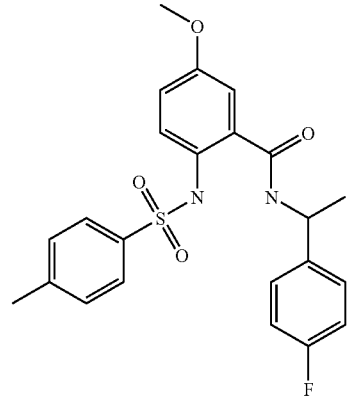 | 443 (M + 1) |

| Example | Structure | Mass |
|---|---|---|
| 105 | 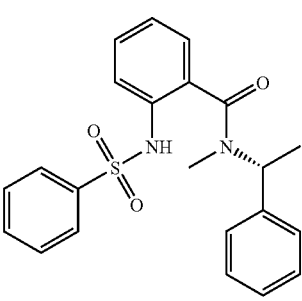 | 395 (M + 1) |
| 106 | 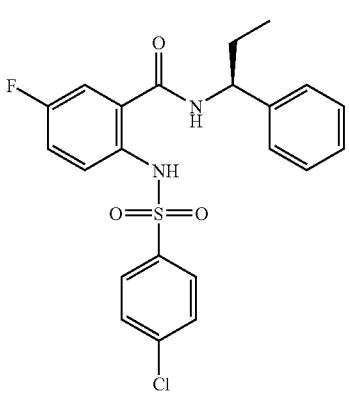 | 447 (M + 1) |
| 107 | 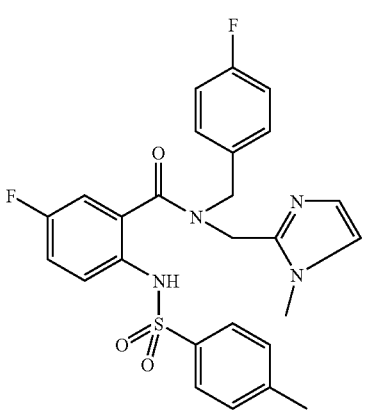 | 511 (M + 1) |
| 108 | 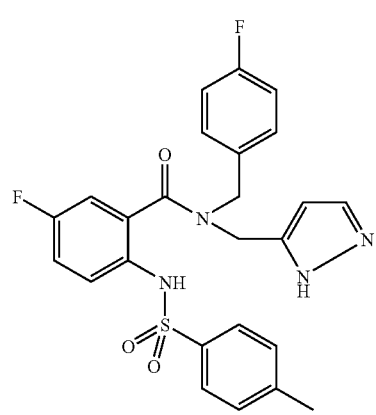 | 497 (M + 1) |
| Example | Structure | Mass |
|---|---|---|
| 109 | 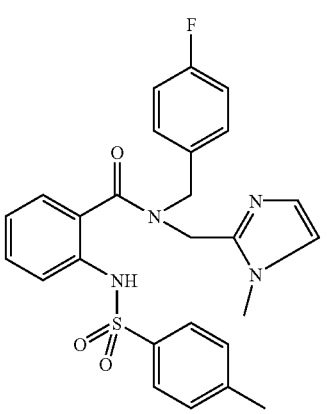 | 493 (M + 1) |
| 110 | 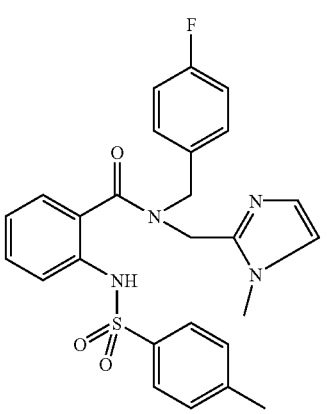 | 496 (M + 1) |
| 111 | 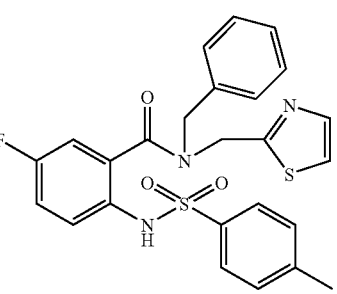 | 473 (M + 1) |
| 112 | 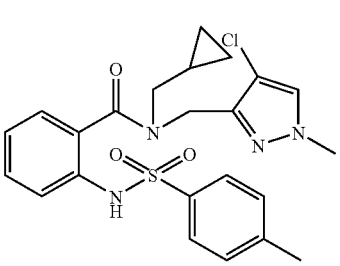 | 461 (M + 1) |
| 113 | 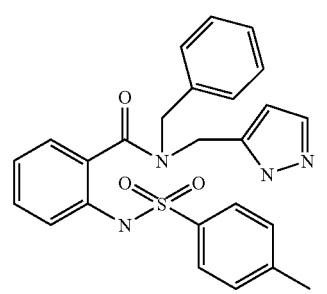 | 450 (M + 1) |

-continued

| Example | Structure | Mass |
|---|---|---|
| 114 | 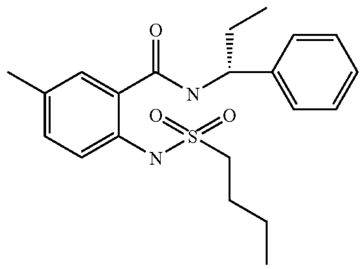 | 389 (M + 1) |
| 115 | 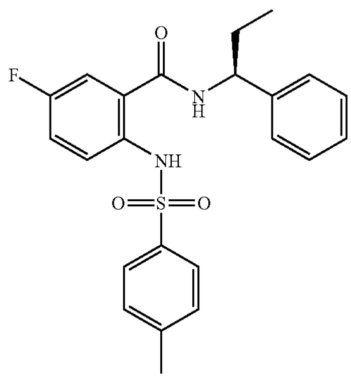 | 427 (M + 1) |
| 116 | 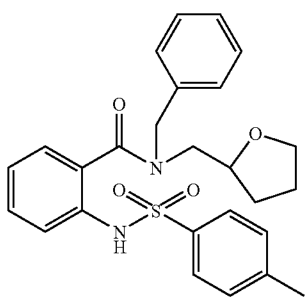 | 465 (M + 1) |

The following further examples were prepared in accordance with general method 5:

| Example | Structure | Mass (ES) |
|---|---|---|
| 117 | 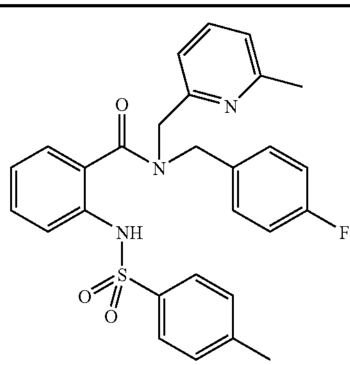 | 504 (M + 1) |

-continued

| Example | Structure | Mass (ES) |
|---|---|---|
| 118 | 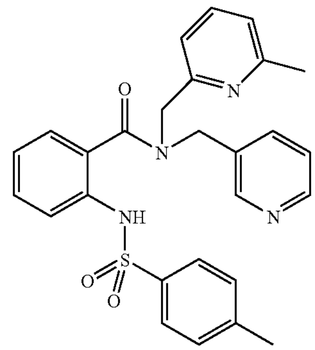 | 487 (M + 1) |
| 119 | 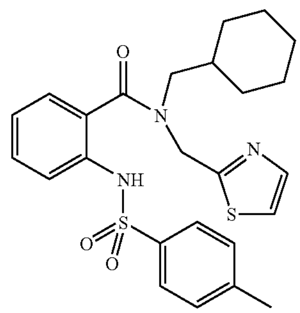 | 484 (M + 1) |
| 120 | 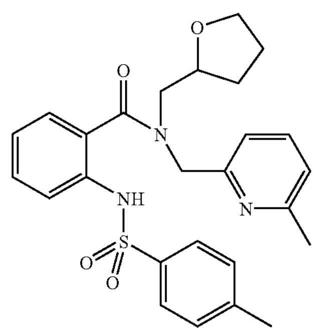 | 480 (M + 1) |
| 121 | 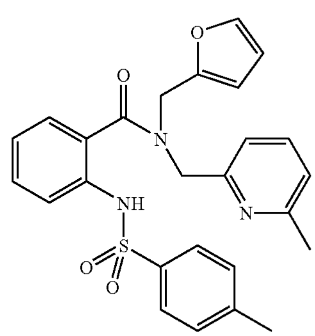 | 476 (M + 1) |

-continued
| Example | Structure | Mass (ES) |
|---|---|---|
| 122 | 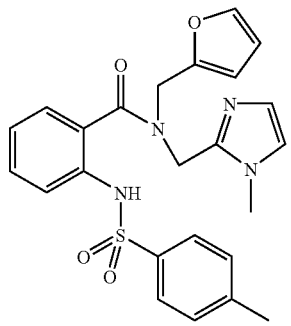 | 465 (M + 1) |
| 123 | 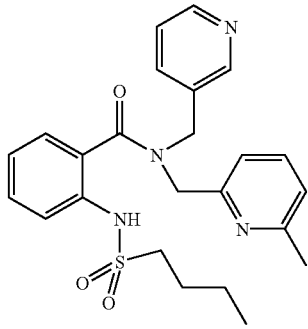 | 453 (M + 1) |
| 124 | 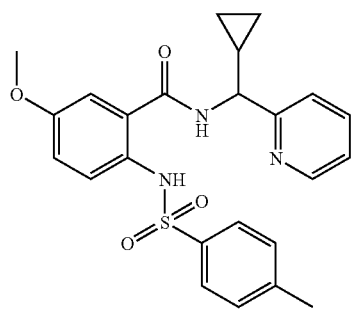 | 452 (M + 1) |
| 125 | 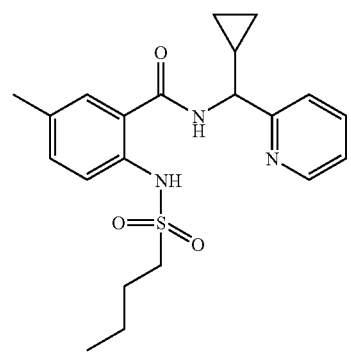 | 402 (M + 1) |
-continued
| Example | Structure | Mass (ES) |
|---|---|---|
| 126 | 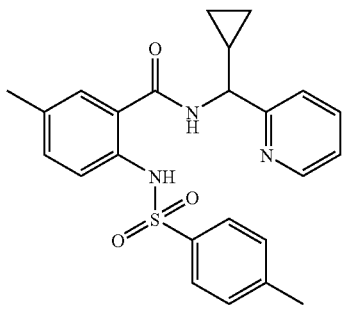 | 436 (M + 1) |
| 127 | 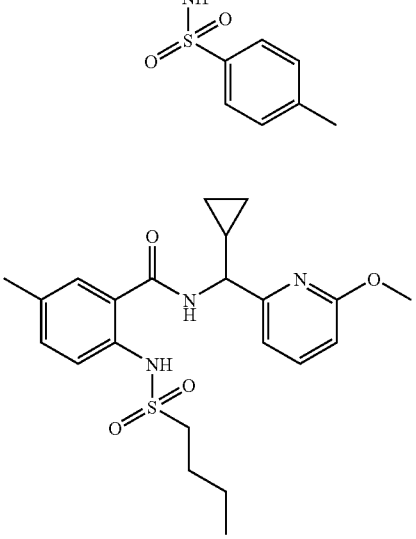 | 432 (M + 1) |
| 128 | 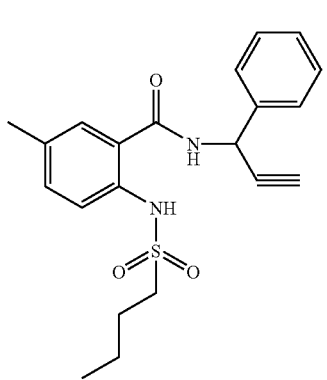 | 385 (M + 1) |
| 129 | 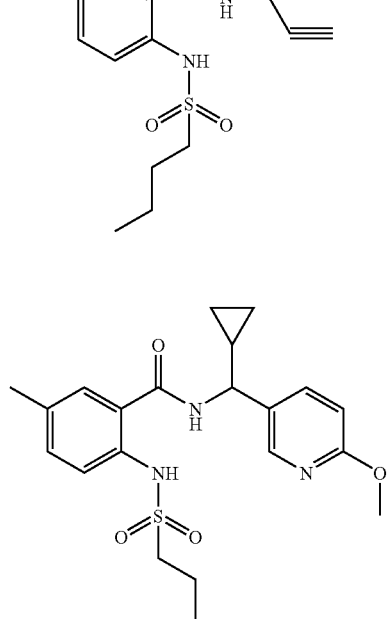 | 432 (M + 1) |

| Example | Structure | Mass (ES) |
|---|---|---|
| 130 | 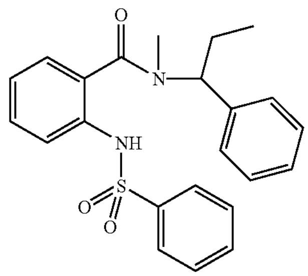 | 409 (M + 1) |
| 131 | 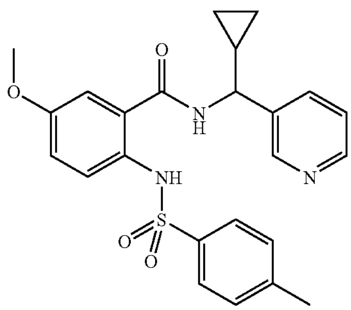 | 452 (M + 1) |
| 132 | 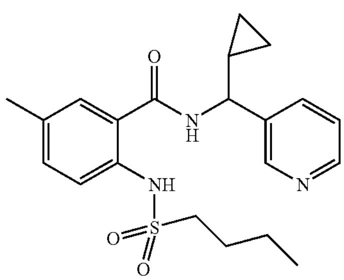 | 402 (M + 1) |
| 133 | 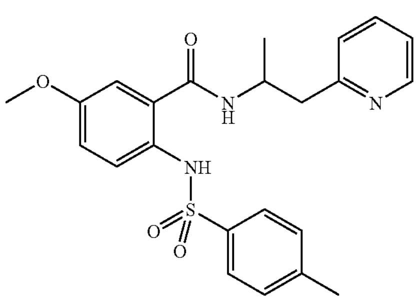 | 440 (M + 1) |
| 134 | 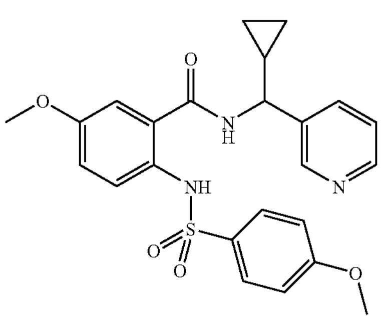 | 468 (M + 1) |
| 135 | | 443 (M + 1) |
| 136 | | 393 (M + 1) |

The following further examples were prepared in accordance with general method 6:

| Example | Structure | Mass (ES) |
|---|---|---|
| 137 | 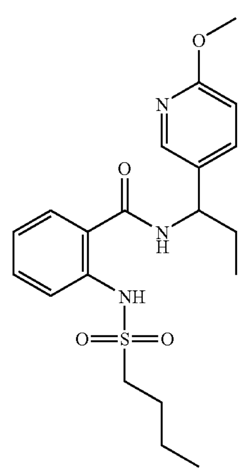 | 406 (M + 1) |

-continued
| Example | Structure | Mass (ES) |
|---|---|---|
| 138 | 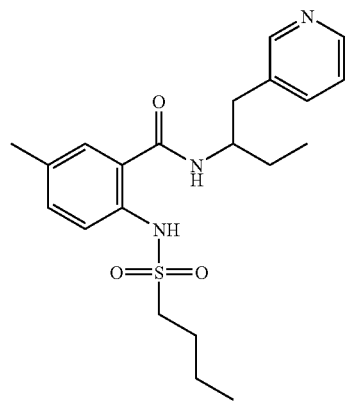 | 404 (M + 1) |
| 139 | 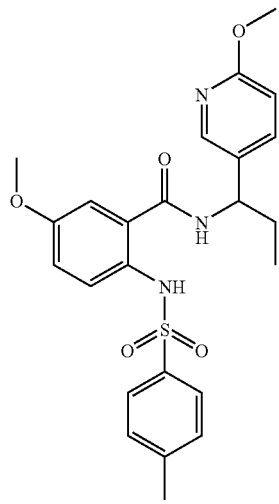 | 470 (M + 1) |
| 140 | 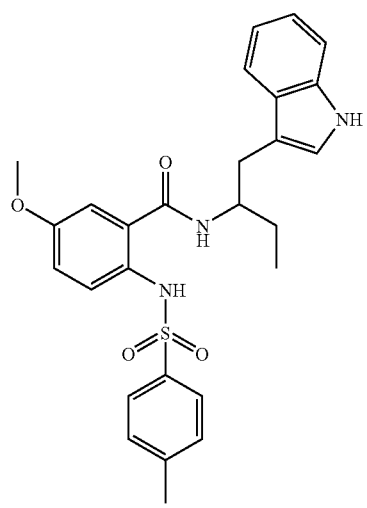 | 492 (M + 1) |
-continued
| Example | Structure | Mass (ES) |
|---|---|---|
| 141 | 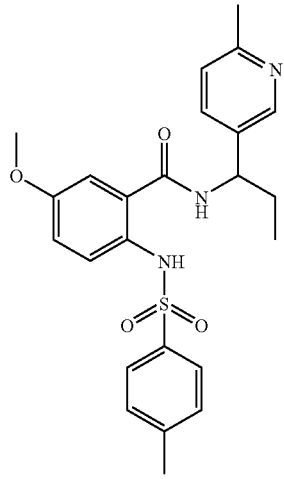 | 454 (M + 1) |
| 142 | 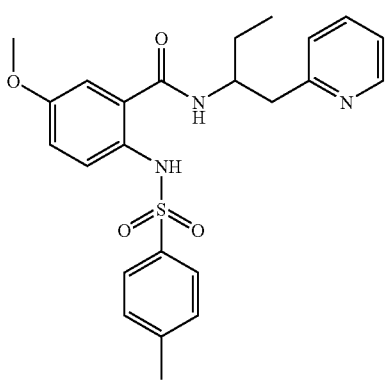 | 454 (M + 1) |
| 143 | 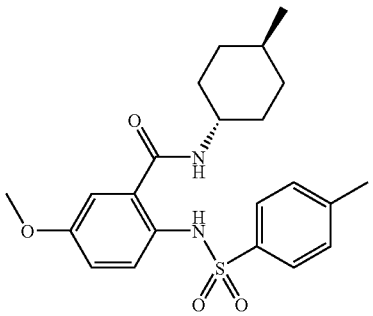 | 417 (M + 1) |
| 144 | 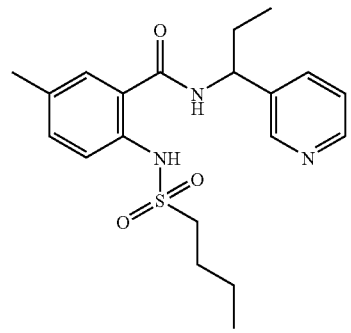 | 390 (M + 1) |

-continued

| Example | Structure | Mass (ES) |
|---|---|---|
| 145 | 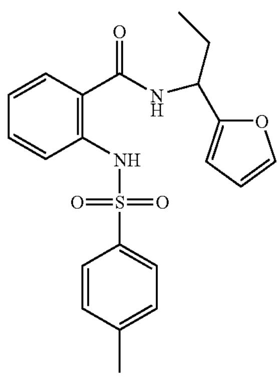 | 399 (M + 1) |

The following further examples were prepared in accordance with general method 7:

| Example | Structure | Mass (ES) |
|---|---|---|
| 146 | 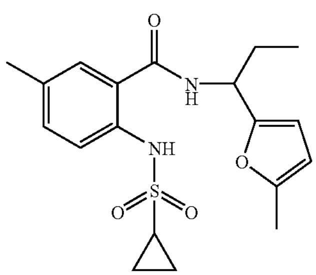 | 377 (M + 1) |
| 147 | 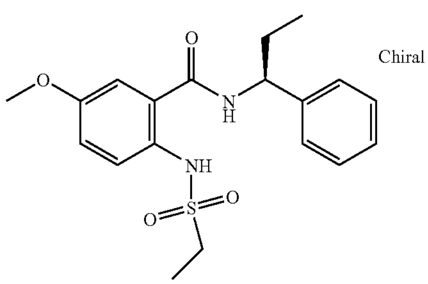 | 377 (M + 1) Chiral |
| 148 | 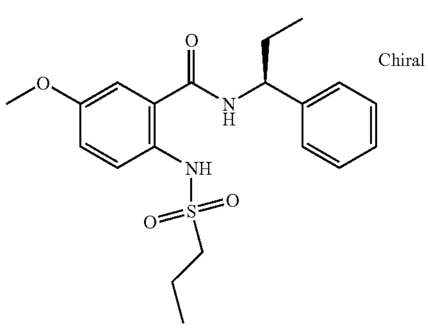 | 391 (M + 1) Chiral |

-continued

| Example | Structure | Mass (ES) |
|---|---|---|
| 149 | 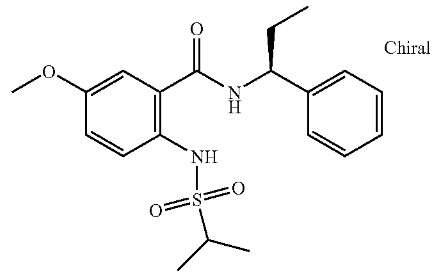 | 391 (M + 1) Chiral |
| 150 | 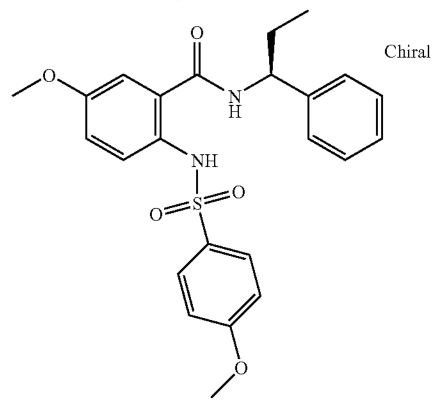 | 455 (M + 1) Chiral |
| 151 | 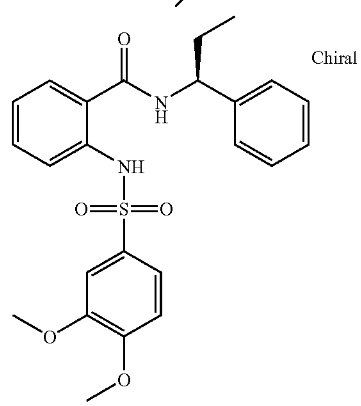 | 455 (M + 1) Chiral |

Example 152
5-Hydroxy-N-(1-phenylpropyl)-2-(toluene-4-sulfonylamino)benzamide

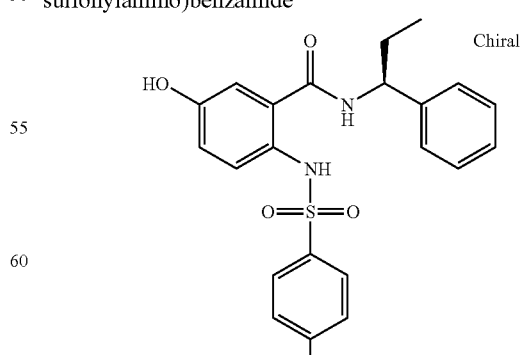

The compound was obtained from the compound of example 90 by cleavage of the methyl ether with boron tribromide.

Example 153
Pharmacological Activity of the Prepared Compounds

Human Kv1.5 channels were expressed in Xenopus oocytes. For this purpose, firstly oocytes were isolated from *Xenopus laevis* and were defolliculated. Kv1.5-encoding RNA which had been synthesized in vitro was then injected into these oocytes. After 1–7 days of Kv1.5 protein expression, the Kv1.5 currents were measured on the oocytes by the two-microelectrode voltage clamp technique. The Kv1.5 channels were for this purpose usually activated with voltage jumps lasting 500 ms to 0 mV and 40 mV. A solution of the following composition flowed through the bath: NaCl 96 mM, KCl 2 mM, $CaCl_2$ 1.8 mM, $MgCl_2$ 1 mM, HEPES 5 mM (titrated to pH 7.4 with NaOH). These experiments were carried out at room temperature. The following were employed for data acquisition and analysis: geneclamp amplifier (Axon Instruments, Foster City, USA) and MacLab D/A converter and software (ADInstruments, Castle Hill, Australia). The compounds of the invention were tested by adding them in various concentrations to the bath solution. The effects of the compounds were calculated as percentage inhibition of the Kv1.5 control current which was obtained when no compound was added to the solution. The data were then extrapolated using the Hill equation in order to determine the inhibitory concentrations $IC_{50}$ for the respective compounds.

The following $IC_{50}$ values were determined in this way for the compounds listed below:

| Example No. | $IC_{50}$ [μM] |
|---|---|
| 1 | 5.5 |
| 2 | 8.2 |
| 3 | 2.8 |
| 4 | 4.1 |
| 5 | 4.5 |
| 6 | 8.2 |
| 7 | 5.1 |
| 8 | 0.9 |
| 9 | 4.9 |
| 10 | 2.5 |
| 11 | 8.0 |
| 12 | 5.4 |
| 13 | 10.0 |
| 14 | 8.5 |
| 15 | 7.8 |
| 16 | 6.4 |
| 17 | 7.5 |
| 18 | 6.7 |
| 19 | 4.2 |
| 20 | 7.7 |
| 21 | 5.2 |
| 22 | 4.8 |
| 23 | 5.0 |
| 24 | 3.0 |
| 25 | 3.4 |
| 26 | 0.6 |
| 27 | 5.6 |
| 28 | 3.2 |
| 29 | 5.1 |
| 30 | 0.7 |
| 31 | 2.6 |
| 32 | 8.5 |
| 33 | 6.5 |
| 34 | 3.1 |
| 35 | 2.0 |
| 36 | 2.0 |
| 37 | 1.9 |
| 38 | 1.6 |
| 39 | >10 |
| 40 | 0.8 |
| 41 | 1.9 |
| 42 | 5.0 |
| 43 | 5.4 |
| 44 | 2.9 |
| 45 | 2.5 |
| 46 | 1.2 |
| 47 | 4.7 |
| 48 | >10 |
| 49 | 6.3 |
| 50 | 0.7 |
| 51 | 3.6 |
| 52 | 3.0 |
| 53 | 2.5 |
| 54 | 4.0 |
| 55 | 4.6 |
| 56 | 10.0 |
| 57 | 5.0 |
| 58 | >10 |
| 59 | 1.7 |
| 60 | 0.7 |
| 61 | 5.6 |
| 62 | 3.5 |
| 63 | 1.7 |
| 64 | 0.6 |
| 65 | 4.8 |
| 66 | 4.0 |
| 67 | 5.8 |
| 68 | 2.9 |
| 69 | 1.3 |
| 70 | 3.8 |
| 71 | 6.9 |
| 72 | 5.0 |
| 73 | 3.1 |
| 74 | 1.7 |
| 75 | 2.9 |
| 76 | 4.7 |
| 77 | 2.6 |
| 78 | 2.7 |
| 79 | 0.7 |
| 80 | 1.2 |
| 81 | 0.4 |
| 82 | 3.2 |
| 83 | 1.9 |
| 84 | 1.0 |
| 85 | 5.2 |
| 86 | 1.8 |
| 87 | 6.0 |
| 88 | 3.9 |
| 89 | 3.2 |
| 90 | 0.5 |
| 91 | 0.8 |
| 92 | 0.9 |
| 93 | 1.1 |
| 94 | 1.0 |
| 95 | 0.7 |
| 96 | 1.0 |
| 97 | 0.9 |
| 98 | 2.0 |
| 99 | 0.9 |
| 100 | 1.6 |
| 101 | 0.9 |
| 102 | 0.7 |
| 103 | 1.4 |
| 104 | 1.0 |
| 105 | 2.6 |
| 106 | 3.8 |
| 107 | 0.9 |
| 108 | 1.2 |
| 109 | 1.1 |
| 110 | 1.0 |
| 111 | 1.7 |
| 112 | 0.5 |
| 113 | 2.6 |
| 114 | 1.4 |
| 115 | 2.4 |
| 116 | 1.1 |
| 117 | 2.4 |
| 118 | 2.2 |
| 119 | 2.7 |

-continued

| Example No. | IC$_{50}$ [μM] |
|---|---|
| 120 | 1.4 |
| 121 | 0.6 |
| 122 | 1.2 |
| 123 | 2.9 |
| 124 | 1.0 |
| 125 | 1.8 |
| 126 | 0.6 |
| 127 | 3.3 |
| 128 | 2.2 |
| 129 | 1.3 |
| 130 | 0.7 |
| 131 | 0.7 |
| 132 | 1.0 |
| 133 | 1.4 |
| 134 | 0.9 |
| 135 | 1.2 |
| 136 | 0.9 |
| 137 | 2.4 |
| 138 | 1.8 |
| 139 | 1.0 |
| 140 | 1.4 |
| 141 | 1.1 |
| 142 | 0.7 |
| 143 | 3.6 |
| 144 | 2.8 |
| 145 | 2.6 |
| 146 | 2.5 |
| 147 | 3.8 |
| 148 | 2.1 |
| 149 | 2.2 |
| 150 | 0.3 |
| 151 | 1.5 |
| 152 | 2.6 |

We claim:

1. A compound of formula I,

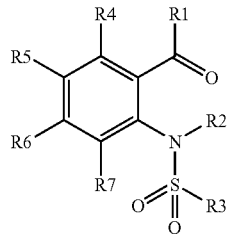

in which:

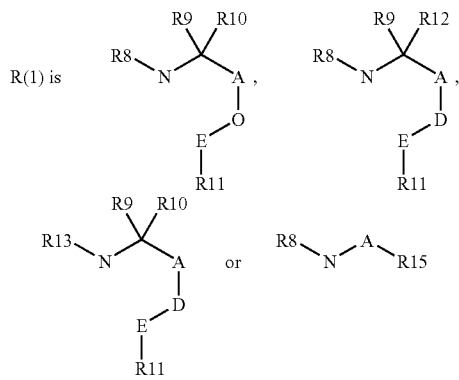

R(1) is

A is —C$_n$H$_{2n}$—;
n is 0, 1, 2, 3, 4 or 5;
O is oxygen;
D is a bond or oxygen;
E is —C$_m$H$_{2m}$—;
m is 0, 1, 2, 3, 4 or 5;
R(8) is hydrogen, alkyl having 1, 2, 3 or 4 carbon atoms or C$_p$H$_{2p}$—R(14);
p is 0, 1, 2, 3, 4 or 5;
R(14) is cycloalkyl having 3, 4, 5 or 6 carbon atoms, aryl or heteroaryl,
where aryl and heteroaryl are unsubstituted or substituted by 1, 2 or 3 substituents selected from the group consisting of F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(9) is hydrogen or alkyl having 1, 2, 3, 4, 5 or 6 carbon atoms;
R(10) is hydrogen, alkyl having 1, 2, 3 or 4 carbon atoms, cycloalkyl having 3, 4, 5 or 6 carbon atoms, aryl or heteroaryl,
where aryl and heteroaryl are unsubstituted or substituted by 1, 2 or 3 substituents selected from the group consisting of F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(11) is cycloalkyl having 3, 4, 5 or 6 carbon atoms, phenyl, naphthyl, thienyl, furyl, pyridyl, pyrazinyl, pyridazinyl or pyrimidyl,
where phenyl, naphthyl, thienyl, furyl, pyridyl, pyrazinyl, pyridazinyl and pyrimidyl are unsubstituted or substituted by 1, 2 or 3 substituents selected from the group consisting of F, Cl, Br, I, CF$_3$, OCF$_3$, NO$_2$, CN, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(12) is alkyl having 1, 2, 3 or 4 carbon atoms, cycloalkyl having 3, 4, 5 or 6 carbon atoms, aryl or heteroaryl,
where aryl and heteroaryl are unsubstituted or substituted by 1, 2 or 3 substituents selected from the group consisting of F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(13) is C$_p$H$_{2p}$—R'(14);
p is 0, 1, 2, 3, 4 or 5;
R'(14) is cycloalkyl having 3, 4, 5 or 6 carbon atoms tetrahydrofuranyl, tetrahydropyranyl, aryl or heteroaryl,
where aryl and heteroaryl are unsubstituted or substituted by 1, 2 or 3 substituents selected from the group consisting of F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(15) is cycloalkyl having 3, 4, 5, 6, 7 or 8 carbon atoms;
R(2) is hydrogen or alkyl having 1, 2, 3 or 4 carbon atoms;
R(3) is alkyl having 3, 4, 5, 6 or 7 carbon atoms, cycloalkyl having 3, 4, 5 or 6 carbon atoms, phenyl or naphthyl,
where phenyl or naphthyl are unsubstitued of substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino; and R(4), R(5), R(6) and R(7) are, independently of one another, selected from the group consisting of hydrogen, F, Cl, Br, I, $CF_3$, $OCF_3$, $OCHF_2$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino; or a pharmaceutically acceptable salt thereof.

2. The compound of claim 1, wherein:

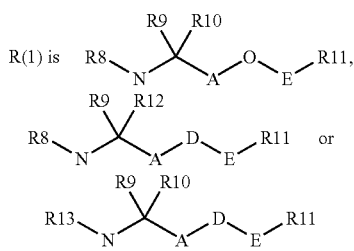

R(1) is

A is —$C_nH_{2n}$—;
n is 0, 1, 2, 3, 4 or 5;
O is oxygen;
D is a bond or oxygen;
E is —$C_mH_{2m}$—;
m is 0, 1, 2, 3, 4 or 5;
R(8) is hydrogen, alkyl having 1, 2, 3 or 4 carbon atoms or $C_pH_{2p}$—R(14);
p is 0, 1, 2, 3, 4 or 5;
R(14) is cycloalkyl having 3, 4, 5 or 6 carbon atoms, aryl or heteroaryl,
where aryl and heteroaryl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(9) is hydrogen or alkyl having 1, 2, 3, 4, 5 or 6 carbon atoms;
R(10) is hydrogen, alkyl having 1, 2, 3 or 4 carbon atoms, cycloalkyl having 3, 4, 5 or 6 carbon atoms, aryl or heteroaryl,
where aryl and heteroaryl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(11) is cycloalkyl having 3, 4, 5 or 6 carbon atoms, phenyl or pyridyl,
where phenyl and pyridyl are unsubstituted or substituted by 1, 2 or 3 substituents selected from the group consisting of F, Cl, Br, I, $CF_3$, $OCF_3$, $NO_2$, CN, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(12) is alkyl having 1, 2, 3 or 4 carbon atoms, cycloalkyl having 3, 4, 5 or 6 carbon atoms, aryl or heteroaryl,
where aryl and heteroaryl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(13) is $C_pH_{2p}$—R'(14);
p is 0, 1, 2, 3, 4 or 5;
R'(14) is cycloalkyl having 3, 4, 5 or 6 carbon atoms, tetrahydrofuranyl, tetrahydropyranyl, aryl or heteroaryl,
where aryl and heteroaryl are unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(2) is hydrogen or alkyl having 1, 2, 3 or 4 carbon atoms;
R(3) is alkyl having 3, 4 or 5 carbon atoms or phenyl,
where phenyl is unsubstituted or substituted by 1, 2 or 3 substituents selected from the group consisting of F, Cl, Br, I, $CF_3$, $OCF_3$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino; and
R(4), R(5), R(6) and R(7) are, independently of one another, selected from the group consisting of hydrogen, F, Cl, Br, I, $CF_3$, $OCF_3$, $OCHF_2$, $NO_2$, CN, COOMe, $CONH_2$, COMe, $NH_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino; or
a pharmaceutically acceptable salt thereof.

3. The compound of claim 1, wherein:

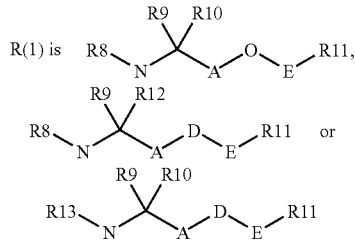

A is —$C_nH_{2n}$—;
n is 0, 1, 2 or 3;
O is oxygen;
D is a bond or oxygen;
E is —$C_mH_{2m}$—;
m is 0, 1, 2 or 3;
R(8) is hydrogen or alkyl having 1, 2, 3 or 4 carbon atoms;
R(9) is hydrogen or alkyl having 1, 2, 3, 4, 5 or 6 carbon atoms;
R(10) is hydrogen, alkyl having 1, 2, 3 or 4 carbon atoms or cycloalkyl having 3, 4 or 5 carbon atoms,
R(11) is cycloalkyl having 3, 4, 5 or 6 carbon atoms, phenyl or pyridyl,
where phenyl and pyridyl are unsubstituted or substituted by 1, 2 or 3 substituents selected from the group consisting of F, Cl, Br, $CF_3$, $OCF_3$, $NO_2$, CN, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(12) is alkyl having 1, 2, 3 or 4 carbon atoms, cycloalkyl having 3, 4 or 5 carbon atoms, aryl or heteroaryl, where aryl and heteroaryl are unsubstituted or substituted by 1, 2 or 3 substituents selected from the group consisting of F, Cl, Br, $CF_3$, $OCF_3$, $NO_2$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(13) is $C_pH_{2p}$—R'(14);

p is 0, 1, 2, 3, 4 or 5;

R'(14) is cycloalkyl having 3, 4, 5 or 6 carbon atoms, tetrahydrofuranyl, tetrahydropyranyl, aryl or heteroaryl, where aryl and heteroaryl are unsubstituted or substituted by 1, 2 or 3 substituents selected from the group consisting of F, Cl, Br, $CF_3$, $OCF_3$, $NO_2$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(2) is hydrogen or alkyl having 1 or 2 carbon atoms;

R(3) is alkyl having 3, 4 or 5 carbon atoms or phenyl, where phenyl is unsubstituted or substituted by 1, 2 or 3 substituents selected from the group consisting of F, Cl, Br, $CF_3$, $OCF_3$, $NO_2$, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino; and R(4), R(5), R(6) and R(7) are, independently of one another, selected from the group consisting of hydrogen, F, Cl, Br, $CF_3$, $OCF_3$, $OCHF_2$, $NO_2$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino; or a pharmaceutically acceptable salt thereof.

4. The compound of claim 1, wherein:

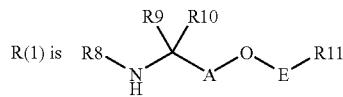

A is —$C_nH_{2n}$—;

n is 0, 1 or 2;

O is oxygen;

E is —$C_mH_{2m}$—;

m is 0 or 1;

R(8) is hydrogen or alkyl having 1, 2, 3 or 4 carbon atoms;

R(9) is hydrogen or alkyl having 1, 2, 3 or 4 carbon atoms;

R(10) is hydrogen or alkyl having 1 or 2 carbon atoms

R(11) is phenyl, where phenyl is unsubstituted or substituted by 1, 2 or 3 substituents selected from the group consisting of F, Cl, $CF_3$, $OCF_3$, CN, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(2) is hydrogen;

R(3) is alkyl having 3, 4 or 5 carbon atoms or phenyl, where phenyl is unsubstituted or substituted by 1, 2 or 3 substituents selected from the group consisting of F, Cl, $CF_3$, $OCF_3$, COOMe, $CONH_2$, COMe, OH,
alkyl having 1, 2, 3 or 4 carbon atoms, alkoxy having 1, 2, 3 or 4 carbon atoms, dimethylamino, sulfamoyl, methylsulfonyl and methylsulfonylamino; and R(4), R(5), R(6) and R(7) are, independently of one another, selected from the group consisting of hydrogen, F, Cl, $CF_3$, $OCF_3$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino; or a pharmaceutically acceptable salt thereof.

5. The compound of claim 1, wherein:

A is —$C_nH_{2n}$—;

n is 0, 1 or 2;

D is a bond or oxygen;

E is —$C_mH_{2m}$—;

m is 0 or 1;

R(8) is hydrogen or alkyl having 1, 2, 3 or 4 carbon atoms;

R(9) is hydrogen or alkyl having 1, 2, 3 or 4 carbon atoms;

R(11) is phenyl or pyridyl, where phenyl and pyridyl are unsubstituted or substituted by 1, 2 or 3 substituents selected from the group consisting of F, Cl, $CF_3$, $OCF_3$, CN, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(12) is alkyl having 1, 2, 3 or 4 carbon atoms or cyclopropyl;

R(2) is hydrogen;

R(3) is alkyl having 3, 4 or 5 carbon atoms or phenyl, where phenyl is unsubstituted or substituted by 1, 2 or 3 substituents selected from the group consisting of F, Cl, $CF_3$, $OCF_3$, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino; and R(4), R(5), R(6) and R(7) are, independently of one another, selected from the group consisting of hydrogen, F, Cl, $CF_3$, $OCF_3$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino; or a pharmaceutically acceptable salt thereof.

6. The compound of claim 1, wherein:

A is —$C_nH_{2n}$—;

n is 0, 1 or 2;

D is a bond or oxygen;

E is —$C_mH_{2m}$—;

m is 0 or 1;

R(9) is hydrogen or alkyl having 1 or 2 carbon atoms;

R(10) is hydrogen or alkyl having 1 or 2 carbon atoms;

R(11) is cycloalkyl having 3, 4, 5 or 6 carbon atoms, phenyl, where phenyl is unsubstituted or substituted by 1, 2 or 3 substituents selected from the group consisting of F, Cl, CF$_3$, OCF$_3$, CN, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(13) is C$_p$H$_{2p}$—R'(14);

p is 0, 1, 2, 3 or 4;

R'(14) is aryl or heteroaryl,
where aryl and heteroaryl are unsubstituted or substituted by 1, 2 or 3 substituents selected from the group consisting of F, Cl, CF$_3$, OCF$_3$, CN, COOMe, CONH$_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R(2) is hydrogen;

R(3) is alkyl having 3, 4 or 5 carbon atoms or phenyl,
where phenyl is unsubstituted or substituted by 1, 2 or 3 substituents selected from the group consisting of F, Cl, CF$_3$, OCF$_3$, COOMe, CONH$_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino; and R(4), R(5), R(6) and R(7) are, independently of one another, selected from the group consisting of hydrogen, F, Cl, CF$_3$, OCF$_3$, CN, COOMe, CONH$_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino; or a pharmaceutically acceptable salt thereof.

7. The compound of claim 1 which is

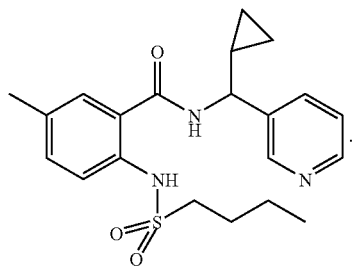

8. The compound of claim 1 which is

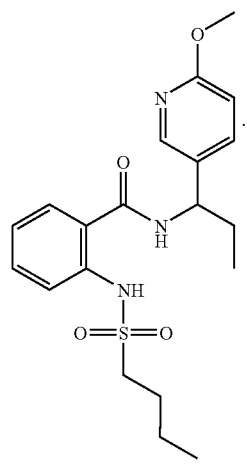

9. A method for the therapy or prophylaxis of cardiac arrhythmias, of supraventricular arrhythmias, of atrial fibrillation or atrial flutters comprising administering an efficacious amount of the compound of claim 7.

10. A pharmaceutical preparation for human or veterinary use comprising an efficacious amount of the compound of claim 7, together with pharmaceutically acceptable vehicles or additives.

11. A method for the therapy or prophylaxis of cardiac arrhythmias, of supraventricular arrhythmias, of atrial fibrillation or atrial flutters comprising administering an efficacious amount of the compound of claim 8.

12. A pharmaceutical preparation for human or veterinary use comprising an efficacious amount of the compound of claim 8, together with pharmaceutically acceptable vehicles or additives.

13. A pharmaceutical composition comprising one or more compounds of claim 1.

14. The pharmaceutical composition of claim 13, further comprising one or more of pharmaceutically acceptable carriers and additives.

15. The pharmaceutical composition of claim 13, further comprising one or more other pharmaceutically active ingredients.

16. A method of treating or preventing a K$^+$ channel-mediated disease comprising administering one or more compounds of claim 1 to a patient in need of such a treatment.

17. The method of claim 16, wherein the disease is a cardiac arrhythmia which can be abolished by prolonging the action potential.

18. The method of claim 16, wherein the disease is a reentry arrhythmia.

19. The method of claim 16, wherein the disease is a supraventricular arrhythmia.

20. The method of claim 16, wherein the disease is an atrial fibrillation or atrial flutter.

21. The pharmaceutical composition of claim 13, further comprising one or more beta-blockers.

22. The pharmaceutical composition of claim 21, further comprising one or more of pharmaceutically acceptable carriers and additives.

23. The pharmaceutical composition of claim 13, further comprising one or more IKs channel blockers.

24. The pharmaceutical composition of claim 23, further comprising one or more pharmaceutically acceptable carriers or additives.

* * * * *